United States Patent
Pouchoulin

(10) Patent No.: US 10,258,726 B2
(45) Date of Patent: Apr. 16, 2019

(54) PROCESS OF CONTROLLING AN APPARATUS FOR EXTRACORPOREAL TREATMENT OF BLOOD

(71) Applicant: GAMBRO LUNDIA AB, Lund (SE)

(72) Inventor: Dominique Pouchoulin, Tramoyes (FR)

(73) Assignee: Gambro Lundia AB, Lund (SE)

( * ) Notice: Subject to any disclaimer, the term of this patent is extended or adjusted under 35 U.S.C. 154(b) by 253 days.

(21) Appl. No.: 15/240,231

(22) Filed: Aug. 18, 2016

(65) Prior Publication Data

US 2016/0354528 A1    Dec. 8, 2016

Related U.S. Application Data

(62) Division of application No. 14/388,295, filed as application No. PCT/IB2013/052275 on Mar. 22, 2013, now abandoned.

(Continued)

(30) Foreign Application Priority Data

Mar. 28, 2012 (EP) .................................... 12002252

(51) Int. Cl.
*A61M 1/16* (2006.01)
*A61M 1/36* (2006.01)
*A61M 1/34* (2006.01)

(52) U.S. Cl.
CPC ............ *A61M 1/1647* (2014.02); *A61M 1/16* (2013.01); *A61M 1/1643* (2014.02); *A61M 1/34* (2013.01);

(Continued)

(58) Field of Classification Search
CPC .................................................. G06F 19/3468
See application file for complete search history.

(56) References Cited

U.S. PATENT DOCUMENTS 5,211,849 A    5/1993  Kitaevich
5,401,238 A *  3/1995  Pirazzoli .................. A61M 1/16
                                                  604/6.11

(Continued)

FOREIGN PATENT DOCUMENTS

| CN | 1761494 | 4/2010 |
|---|---|---|
| TW | 41938 | 1/2001 |
| WO | WO 98/50091 | 11/1998 |

OTHER PUBLICATIONS

PCT Search Report and Written Opinion for PCT/IB2013/052275 dated Jun. 18, 2013 (14 pages).

*Primary Examiner* — Krishnan S Menon
*Assistant Examiner* — Ryan B Huang
(74) *Attorney, Agent, or Firm* — Mueting, Raasch & Gebhardt, P.A.

(57) ABSTRACT

An apparatus for extracorporeal treatment of blood (1) comprising a filtration unit (2), a blood withdrawal line (6), a blood return line (7), an effluent fluid line (13), a pre and/or post-dilution fluid line (15, 25) connected to the blood withdrawal line, and a dialysis fluid line. Pumps (17, 18, 21, 22, 27) act on the fluid lines for regulating the flow of fluid. A control unit (10) is configured to periodically calculate a new value for the patient fluid removal rate to be imposed on an ultrafiltration actuator in order to keep a predefined patient fluid removal rate across a reference time interval irrespective of machine down times.

18 Claims, 6 Drawing Sheets

Related U.S. Application Data

(60) Provisional application No. 61/616,519, filed on Mar. 28, 2012.

(52) U.S. Cl.
CPC .......... *A61M 1/341* (2014.02); *A61M 1/3403* (2014.02); *A61M 1/3413* (2013.01); *A61M 1/3434* (2014.02); *A61M 1/3441* (2013.01); *A61M 1/3451* (2014.02); *A61M 1/3638* (2014.02); *A61M 2205/18* (2013.01); *A61M 2205/3334* (2013.01); *A61M 2205/3393* (2013.01); *A61M 2205/505* (2013.01); *A61M 2205/52* (2013.01)

(56) References Cited

U.S. PATENT DOCUMENTS

| | | |
|---|---|---|
| 2004/0182787 A1 | 9/2004 | Chevallet |
| 2004/0267183 A1 | 12/2004 | Chevallet |
| 2006/0124548 A1* | 6/2006 | Okazaki ............... A61M 1/16 210/646 |
| 2008/0154170 A1 | 6/2008 | Lannoy |
| 2009/0101550 A1 | 4/2009 | Muller |

* cited by examiner

PROCESS OF CONTROLLING AN APPARATUS FOR EXTRACORPOREAL TREATMENT OF BLOOD

This application is a divisional of U.S. Ser. No. 14/388,925 having a 371(c) date of Sep. 26, 2014 (hereby incorporated by reference in its entirety), which is a U.S. National Stage Application of International Application No. PCT/IB2013/052275, filed Mar. 22, 2013, which was published in English on Oct. 3, 2013 as International Patent Publication WO 2013/144793 A1, which claims the benefit under 35 U.S.C. 119(e) of U.S. Provisional Application No. 61/616,519 filed Mar. 28, 2012. International Application No. PCT/IB2013/052275 also claims priority to European Application No. 12002252.0 filed Mar. 28, 2012.

DESCRIPTION

The present invention relates to an apparatus for extracorporeal treatment of blood.

Extracorporeal blood treatment involves removing blood from a patient, treating the blood externally to the patient, and returning the treated blood to the patient. Extracorporeal blood treatment is typically used to extract undesirable matter or molecules from the patient's blood and add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood, to maintain an acid/base balance or to remove excess body fluids, for example.

Extracorporeal blood treatment is typically accomplished by removing the blood from the patient in e.g. a continuous flow, introducing the blood into a primary chamber, also referred to as blood chamber, of a filtration unit (such as a dialyzer or an hemofilter) where the blood is allowed to flow past a semipermeable membrane. The semipermeable membrane selectively allows matter in the blood to cross the membrane from the primary chamber into a secondary chamber and also selectively allows matter in the secondary chamber to cross the membrane into the blood in the primary chamber, depending on the type of treatment.

A number of different types of extracorporeal blood treatments may be performed. In an ultrafiltration (UF) treatment, undesirable matter is removed from the blood by convection across the membrane into the secondary chamber. In a hemofiltration (HF) treatment, the blood flows past the semipermeable membrane as in UF and desirable matter is added to the blood, typically by dispensing a fluid into the blood either before and/or after it passes through the filtration unit and before it is returned to the patient. In a hemodialysis (HD) treatment, a secondary fluid containing desirable matter is introduced into the secondary chamber of the filtration unit. Undesirable matter from the blood crosses the semipermeable membrane into the secondary fluid and desirable matter from the secondary fluid may cross the membrane into the blood. In a hemodiafiltration (HDF) treatment, blood and secondary fluid exchange matter as in HD, and, in addition, matter is added to the blood, typically by dispensing a fluid into the treated blood before its return to the patient as in HF.

Specific blood treatment apparatus have been developed for the treatment of acute patients mainly because:

it is not known how long these patients will suffer from kidney insufficiency; thus, the total treatment time is a priori unknown and, as such, it may not be used as setup parameter;

in fact, intensive care apparatus used for treating acute patient are designed to request flow rate information as setup parameters;

moreover, acute patients need relatively long treatment sessions, typically lasting several days, during which the blood treatment apparatus is a master piece of the patient fluid balance management, allowing for accurate balancing of the multiple infusions generally present (drugs, fluids, nutrition);

furthermore, acute patients often need to be treated in emergency situations, thus apparatus for acute treatment shall be characterized by easy and safe set up procedures.

In this situation, blood treatment apparatus have been developed presenting infusion lines for supplying fluid upstream or downstream the filtration unit, a fresh dialysis liquid line for supplying liquid to the dialysate chamber of the filtration unit, and a waste line receiving spent dialysis fluid and ultrafiltered fluid from filtration unit. In correspondence of each of the above lines, means for generating a flow rate is acting, such as a peristaltic pump which is rotated under the supervision of a control unit. Moreover, fluid containers supply fluid to the infusion lines and to the dialysate line, while a waste container or a waste handling system receives the spent liquid from the waste line. Typically, scales are used to weigh the fluid containers and to provide signals used by the control unit to control the pumps or other actuators on the fluid lines so that the apparatus achieves the fluid removal rate set by the user, and—depending upon the apparatus—any other rates through each line. In more sophisticated solutions, each of the above lines receives fluid from a respective container which, in use, is associated to a respective scale and cooperates with a respective pump. A user interface allows an operator entering the patient fluid removal rate and the fluid flow rates of each of the substitution lines and dialysate line such that the apparatus is capable of continuously keep under control the amount of fluid infused, the amount of fluid flowing through the dialysate line and the fluid loss rate.

Although the above solution results in efficient apparatus able to perform all necessary treatments and to accurately control the flows, the applicant has found ways to further improve known blood treatment apparatuses.

It is an object of the present invention to render available a blood treatment apparatus suitable for intensive care applications which may be automatically able to account for down times or interruption in the treatment delivery.

More in detail, it is an object of the invention an apparatus which is able to take into account the effective portions of the treatment procedure, adapting certain set-up parameters to account for machine stops, therapy delivery interruptions, machine downtimes.

An auxiliary object is an apparatus able to control patient fluid removal rate across long treatments, without compromising the operating philosophy of an intensive care apparatus.

Another object is an apparatus capable of operating in a safe manner.

Another object is to automatically ascertain whether certain prescription targets cannot be achieved and inform the operator accordingly.

SUMMARY

At least one of the above objects is substantially reached by an apparatus according to one or more of the appended claims.

Apparatus and processes for the extracorporeal treatment of blood according to aspects of the invention are here below described.

A 1st aspect relates to an apparatus for extracorporeal treatment of blood comprising: a filtration unit (2) having a primary chamber (3) and a secondary chamber (4) separated by a semi-permeable membrane (5); a blood withdrawal line (6) connected to an inlet of the primary chamber (3), and a blood return line (7) connected to an outlet of the primary chamber (4) said blood lines being designed to be connected to a patient cardiovascular system; a blood pump (11) for controlling the flow of blood through the blood lines (6, 7); an effluent fluid line (13) connected to an outlet of the secondary chamber (4); an ultrafiltration actuator connected to the effluent fluid line (13) and configured to cause a transfer of fluid from the primary (3) to the secondary chamber (4), and a control unit (10) configured to control the ultrafiltration actuator based on a set value ($Q_{pfr\_set}$) for patient fluid removal rate, said set value ($Q_{pfr\_set}$) being a desired value for the rate of fluid removal from the patient, wherein the control unit (10) is configured to execute at check points ($T_i$) during patient treatment a control procedure comprising:
  receiving one check information selected in the group of:
    a value of fluid removed from the patient ($V_{pfr\_removed}$; $V_{pfr(0)}$) over a time period ($T_i - T_{retro}$ to $T_i$) preceding a check point ($T_i$),
    an effective time portion, of said time period ($T_i - T_{retro}$ to $T_i$) preceding a check point ($T_i$), during which said ultrafiltration actuator is operated,
    a down time portion, of said time period ($T_i - T_{retro}$ to $T_i$) preceding a check point ($T_i$), during which said ultrafiltration actuator is not operated,
  calculating an updated value ($Q_{pfr\_new}$) for said fluid removal rate ($Q_{pfr}$) as a function of said set value for a fluid removal rate ($Q_{pfr\_set}$) and of said check information.

In a 2$^{nd}$ aspect according to the 1$^{st}$ aspect, the control procedure further comprises, after calculation of said updated value ($Q_{pfr\_new}$), controlling the ultrafiltration actuator after the check point as a function of said updated value ($Q_{pfr\_new}$) for the fluid removal rate. In practice a new $Q_{eff}$ is calculated using (e.g. in formulas (1), (2) or (3)) $Q_{pfr\_new}$ in place of $Q_{pfr\_set}$; and then used to control the ultrafiltration actuator, namely the wast pump positioned on the effluent line exiting from the second chamber.

In a 3$^{rd}$ aspect according to any one of 1$^{st}$ or 2$^{nd}$ aspect, the control procedure further comprises controlling the ultrafiltration actuator, after the check point and until either a subsequent check point as a function of said updated value ($Q_{pfr\_new}$) for the fluid removal rate.

In a 4$^{th}$ aspect according to any one of 1$^{st}$ or 2$^{nd}$ or 3$^{rd}$ aspect the control unit (10) is configured for re-executing said control procedure at a plurality of check points (Ti) during patient treatment, said plurality of check points being one or more in the group of:
  check points at regular intervals,
  periodic check points,
  check points triggered by specific setting of a new set value ($Q_{pfr\_set}$) for patient fluid removal rate,
  check points triggered by a stop in the ultrafiltration actuator,
  check points triggered by each time a flow rate setting is changed.

In a 5$^{th}$ aspect according to any one of the preceding aspects, the control procedure comprises:
  determining a value of the fluid removed from the patient ($V_{pfr\_removed}$) over a time period ($T_{retro}$) preceding a check point ($T_i$);
  determining a value of fluid to be removed from the patient ($V_{pfr\_need}$) over a time period ($T_{prosp}$) following the check point ($T_i$) in order to achieve the set value ($Q_{pfr\_set}$) for fluid removal rate ($Q_{pfr}$) over the the sum of the time period ($T_{retro}$) preceding check point ($T_i$) and of the time period ($T_{prosp}$) following the check point ($T_i$);
  calculating the updated value ($Q_{pfr\_new}$) for said fluid removal rate ($Q_{pfr}$) based on said set value for a fluid removal rate ($Q_{pfr\_set}$), on said value of fluid to be removed from the patient ($V_{pfr\_need}$) over the time period ($T_{prosp}$) following the check point ($T_i$) and on the duration the time period ($T_{prosp}$) following the check point ($T_i$).

In a 6$^{th}$ aspect according to any one of the preceding aspects, the control procedure comprises calculating the updated value ($Q_{pfr\_new}$) for said fluid removal rate ($Q_{pfr}$) at check point ($T_i$) according to the formula:

$$Q_{pfr\_new} = [(T_{retro} + T_{prosp}) \cdot Q_{pfr\_set} - V_{pfr\_removed}]/T_{prosp}$$

where:
  $Q_{pfr\_set}$ is the set value for fluid removal rate;
  $V_{pfr\_removed}$ is the value of the fluid removed from the patient over time period ($T_{retro}$) preceding a check point ($T_i$);
  $T_{retro}$ is a time period preceding check point ($T_i$);
  $T_{prosp}$ is a time period following the check point ($T_i$);
  ($T_{retro} + T_{prosp}$) is the sum of the time period ($T_{retro}$) preceding check point ($T_i$) and of the time period ($T_{prosp}$) following the check point ($T_i$).

In a 7$^{th}$ aspect according to any one of the preceding aspects, each reference time interval ($\Delta T$) is of prefixed duration, beginning at prefixed start times ($T_{00}$; $T_{00} + \Delta T$; . . . ; $T_{00} + k \cdot \Delta T$) and ending at prefixed ending times ($T_{00} + \Delta T$; $T_{00} + 2\Delta T$; . . . ; $T_{00} + (k+1) \cdot \Delta T$).

In a 8$^{th}$ aspect according to the 7$^{th}$ aspect the control procedure comprises calculating the updated value ($Q_{pfr\_new}$) for said fluid removal rate ($Q_{pfr}$) at check point ($T_i$) comprised between a start time ($T_{00} + k \cdot \Delta T$) and an end time $T_{00} + (k+1) \cdot \Delta T$ according to the formula:

$$Q_{pfr\_new} = (\Delta T \cdot Q_{pfr\_set} - V_{pfr(0)})/[(T_{00} + (k+1) \cdot \Delta T) - T_i]$$

or $$Q_{pfr\_new} = (2 \cdot \Delta T \cdot Q_{pfr\_set} - V_{pfr(0)} - V_{pfr(k-1)})/[(T_{00} + (k+1) \cdot \Delta T) - T_i]$$

where:
  $Q_{pfr\_set}$ is the set value for fluid removal rate;
  $V_{pfr(0)}$ is the value of the fluid removed from the patient over time window running from ($T_{00} + k \cdot \Delta T$) to check point ($T_i$);
  $V_{pfr(k-1)}$ is the value of the fluid removed from the patient over time window running from ($T_{00} + (k-1) \cdot \Delta T$) to ($T_{00} + k \cdot \Delta T$);
  [($T_{00} + (k+1) \cdot \Delta T) - T_i$] is the duration of time period following the check point ($T_i$); $\Delta T$ is the reference time interval.

In a 9$^{th}$ aspect according to any one of the preceding aspects, the control procedure comprises:

determining an effective portion ($T_{eff}$) of said the time period ($T_{prosp}$; [$T_{00}$+(k+1)·$\Delta T$)−$T_i$]) following the check point ($T_i$), during which it is forecasted that the ultrafiltration actuator will be actually pulling fluid from the primary into the secondary chamber (4);

calculating the updated value ($Q_{pfr\_new}$) for said fluid removal rate ($Q_{pfr}$) using said effective portion ($T_{eff}$) in place of the duration the time period following the check point ($T_i$).

In a $10^{th}$ aspect according to any one of the preceding aspects the effective portion ($T_{eff}$) is calculated reducing the duration of said the time period following check point ($T_i$) by a quantity linked to the number of bag changes expected in the next time period.

In a $11^{th}$ aspect according to any one of the preceding aspects the effective portion ($T_{eff}$) is calculated reducing the duration of said the time period following check point ($T_i$) by a quantity linked to down times caused by alarm conditions.

In a $12^{th}$ aspect according to any one of the preceding aspects from the $5^{th}$ to the $11^{th}$ the effective portion ($T_{eff}$) is calculated reducing the duration of said the time period following check point ($T_i$) by a quantity 11 linked to down times caused by alarm conditions if the duration of the time period ($T_{prosp}$) following the check point ($T_i$) is greater than a prefixed duration, such as grater than 30 mins or grater than 60 mins.

In a $13^{th}$ aspect according to any one of the preceding aspects, the control unit is configured for receiving the set value ($Q_{pfr\_set}$) for patient fluid removal rate from an operator's input or from a remote source communicatively connected to the control unit or for pre-storing said set value.

In a $14^{th}$ aspect according to any one of the preceding aspects, the apparatus further comprises a user interface (12) connected to the control unit (10), said control unit being configured to execute the following before executing the control procedure:

display on the user interface an indicium prompting a user to select a set value ($Q_{pfr\_set}$) for the patient fluid removal rate ($Q_{pfr}$), detect entry by the user of the set value ($Q_{pfr\_set}$) for the patient fluid removal rate ($Q_{pfr}$), receive the entered set value ($Q_{pfr\_set}$) for the patient fluid removal rate ($Q_{pfr}$).

In a $15^{th}$ aspect according to any one of the preceding aspects, the apparatus further comprises a pre-dilution fluid line (15) connected to the blood withdrawal line and a pre-dilution pump (18) connected to the control unit (10) and acting on the pre-dilution line for regulating the flow through said pre-dilution fluid.

In a $16^{th}$ aspect according to any one of the preceding aspects, the apparatus further comprises a post-dilution fluid line (25) connected to the blood return line and a post-dilution pump (27) connected to the control unit (10) and acting on the post-dilution line for regulating the flow through said post-dilution fluid line.

In a $17^{th}$ aspect according to any one of the preceding aspects, the apparatus further comprises a dialysis fluid line (19) connected to the inlet of the secondary chamber and a dialysis fluid pump (21) connected to the control unit (10) and acting on the dialysis liquid line for regulating the flow through said dialysis fluid line.

In a $18^{th}$ aspect according to any one of the preceding aspects, the apparatus further comprises a pre-blood pump infusion line (22) connected to the blood withdrawal line in a region of this latter which is positioned in use upstream the blood pump, a pre-blood infusion pump (24) connected to the control unit (10) and acting on the pre-blood pump infusion line for regulating the flow through said pre-blood pump infusion line.

In a $19^{th}$ aspect according to any one of the preceding aspects from the $15^{th}$ to the $18^{th}$ said control unit is configured to receive set values for one or more fluid flow rates selected in the group including a fluid flow rate ($Q_{eff}$) through the effluent line (13), a fluid flow rate ($Q_{rep}$, $Q_{pbp}$) through the infusion fluid line (15, 22, 25), a fluid flow rate ($Q_{dial}$) through the dialysis liquid fluid line (19), in addition to said fluid removal rate ($Q_{pfr}$) from the patient and to control said pumps and said actuator based on the set values for said one or more fluid flow rates and for said fluid removal rate ($Q_{pfr}$) from the patient.

In a $20^{th}$ aspect according to any one of the preceding aspects from the $15^{th}$ to the $18^{th}$, the apparatus further comprises a syringe pump connected to the blood withdrawal line and/or a syringe pump connected to the blood return line said control unit is configured to receive set values for the fluid flow rates through the syringe pump or syringe pumps and to control said infusion pumps, said dialysis pump and said ultrafiltration actuator based on the set values for said one or more fluid flow rates, for said fluid removal rate ($Q_{pfr}$) from the patient, and on the set flow rates for the syringe pumps. In practice each line is controlled based on the respective set flow rate, except for the effluent line where the ultrafiltration actuator (e.g. a pump) is controlled based on the $Q_{eff}$ calculated using formulas (1), (2) or (3) described below in the detailed description, adopting $Q_{pfr\_new}$ in place of $Q_{pfr\_set}$.

In a $21^{st}$ aspect according to any one of the preceding aspects the control procedure comprises requesting the user, optionally via the user interface, to confirm that the calculated updated value ($Q_{pfr\_new}$) for said fluid removal rate ($Q_{pfr}$) is acceptable before using it for controlling the ultrafiltration actuator.

In a $22^{nd}$ aspect according to any one of the preceding aspects the control procedure comprises comparing the calculated updated value ($Q_{pfr\_new}$) for said fluid removal rate ($Q_{pfr}$) against a maximum threshold value before using it for controlling the ultrafiltration actuator.

In a $23^{rd}$ aspect according to any one of the preceding aspects the control procedure comprises executing one or more of the following safety checks:

comparing the ratio between the calculated updated value and the set value for the patient fluid removal rate with a first boundary condition (typically to ±30%), comparing the absolute difference between the calculated updated value and the set value for the patient fluid removal rate with a second boundary condition (typically by ±100 ml/h), comparing the absolute difference between the calculated updated value and the set value for the patient fluid removal rate as a function of patient body weight with a third boundary condition (typically by 0.1 ml/min/kg), wherein the control procedure comprises verifying that a prefixed number, optionally all, of said checks is positively passed before using the update value for controlling the ultrafiltration actuator, optionally wherein said control unit is configured for allowing setting of one or more of said boundary conditions.

In a $24^{th}$ aspect according to any one of the preceding aspects the ultrafiltration actuator comprises a waste pump (17) acting on the effluent conduit (13), this latter leading to a waste container (14) configured for collecting fluid extracted from the secondary chamber (4);

at least one sensor (33) being associated to the waste container and being communicatively connected to the control unit, wherein the sensor is configured to:
   determine the weight or the volume of the fluid in said waste container and
   generate corresponding measurement signals ($W_i$) for the control unit,
and wherein the control unit (10) is configured to calculate the actual quantity of fluid removed from the patient ($V_{pfr}$) over the reference time interval based at least on said measurement signals ($W_i$) coming from the sensor.

In a 25$^{th}$ aspect according to the preceding aspect, the apparatus comprises one or more of the following containers:
   a pre-dilution fluid container connected to the pre-dilution line (15),
   a post-dilution fluid container connected to the post-dilution fluid line (25),
   a dialysis fluid container connected to the dialysis fluid line (19),
   a pre-blood pump infusion fluid container connected to the pre-blood pump infusion (22) line, a respective weighing sensor (34, 37, 35, 36) associated to each one of the above fluid containers and connected to the control unit (10),
   wherein said control unit is configured to receive set values for one or more fluid flow rates selected in the group including a fluid flow rate ($Q_{eff}$) through the effluent line (13), a fluid flow rate ($Q_{rep}$, $Q_{pbp}$) through the infusion fluid line (15, 21, 25), a fluid flow rate ($Q_{dial}$) through the dialysis liquid fluid line (27), in addition to said fluid removal rate ($Q_{pfr}$) from the patient, weigh signals ($W_i$) from said weighing sensors and to control said pumps and said actuator based on said weight signals, the set values for said one or more fluid flow rates and for said fluid removal rate ($Q_{pfr}$) from the patient.

In a 26$^{th}$ aspect according to the preceding aspect, the apparatus comprises the following containers:
   a pre-dilution fluid container connected to the pre-dilution line (15),
   a post-dilution fluid container connected to the post-dilution fluid line (25),
   a dialysis fluid container connected to the dialysis fluid line (19),
   a respective weighing sensor associated to each one of the above fluid containers and connected to the control unit (10),
   wherein said control unit is configured to receive set values for a fluid flow rate ($Q_{eff}$) through the effluent line (13), a fluid flow rate ($Q_{rep}$) through the infusion fluid line, a fluid flow rate ($Q_{dial}$) through the dialysis liquid fluid line, in addition to said fluid removal rate ($Q_{pfr}$) from the patient, weigh signals ($W_i$) from said weighing sensors and
   to control said pumps and said actuator based on said weight signals, the set values for said fluid flow rates and for said fluid removal rate ($Q_{pfr}$) from the patient.

A 27$^{th}$ aspect relates to a process for controlling an apparatus for extracorporeal treatment of blood, the apparatus being of the type comprising: a filtration unit (2) having a primary chamber (3) and a secondary chamber (4) separated by a semi-permeable membrane (5); a blood withdrawal line (6) connected to an inlet of the primary chamber (3), and a blood return line (7) connected to an outlet of the primary chamber (4) said blood lines being designed to be connected to a patient cardiovascular system; a blood pump (11) for controlling the flow of blood through the blood lines (6, 7); an effluent fluid line (13) connected to an outlet of the secondary chamber (4); an ultrafiltration actuator connected to the effluent fluid line (13) and configured to cause a transfer of fluid from the primary (3) to the secondary chamber (4). The process, which may for instance be executed by a control unit, includes the steps of:
   controlling the ultrafiltration actuator based on a set value ($Q_{pfr\_set}$) for patient fluid removal rate, said set value ($Q_{pfr\_set}$) being a desired value for the rate of fluid removal from the patient,
   executing at check points ($T_i$) during patient treatment a control procedure comprising:
      receiving one check information selected in the group of:
         a value of fluid removed from the patient ($V_{pfr\_removed}$; $V_{pfr(0)}$) over a time period ($T_i - T_{retro}$ to $T_i$) preceding a check point ($T_i$),
         an effective time portion, of said time period ($T_i - T_{retro}$ to $T_i$) preceding a check point ($T_i$), during which said ultrafiltration actuator is operated,
         a down time portion, of said time period ($T_i - T_{retro}$ to $T_i$) preceding a check point ($T_i$), during which said ultrafiltration actuator is not operated,
      calculating an updated value ($Q_{pfr\_new}$) for said fluid removal rate ($Q_{pfr}$) as a function of said set value for a fluid removal rate ($Q_{pfr\_set}$) and of said check information.

In a 28$^{th}$ aspect according to the 27$^{th}$ aspect, the control procedure further comprises, after calculation of said updated value ($Q_{pfr\_new}$), controlling the ultrafiltration actuator after the check point as a function of said updated value ($Q_{pfr\_new}$) for the fluid removal rate. In practice a new $Q_{eff}$ is calculated using (e.g. in formulas (1), (2) or (3)) $Q_{pfr\_new}$ in place of $Q_{pfr\_set}$; and then used to control the ultrafiltration actuator, namely the waste pump positioned on the effluent line exiting from the second chamber.

In a 29$^{th}$ aspect according to any one of the preceding 2 aspects, the control procedure further comprises controlling the ultrafiltration actuator, after the check point and until either a subsequent check point as a function of said updated value ($Q_{pfr\_new}$) for the fluid removal rate.

In a 30$^{th}$ aspect according to any one of the preceding 3 aspects comprising re-executing said control procedure at a plurality of check points (Ti) during patient treatment, said plurality of check points being one or more in the group of:
   check points at regular intervals,
   periodic check points,
   check points triggered by specific setting of a new set value ($Q_{pfr\_set}$) for patient fluid removal rate,
   check points triggered by a stop in the ultrafiltration actuator,
   check points triggered by each time a flow rate setting is changed.

In a 31$^{st}$ aspect according to any one of the preceding 4 aspects, the control procedure comprises:
   determining a value of the fluid removed from the patient ($V_{pfr\_removed}$) over a time period ($T_{retro}$) preceding a check point ($T_i$);
   determining a value of fluid to be removed from the patient ($V_{pfr\_need}$) over a time period ($T_{prosp}$) following the check point ($T_i$) in order to achieve the set value ($Q_{pfr\_set}$) for fluid removal rate ($Q_{pfr}$) over the sum of the time period ($T_{retro}$) preceding check point ($T_i$) and of the time period ($T_{prosp}$) following the check point ($T_i$);
   calculating the updated value ($Q_{pfr\_new}$) for said fluid removal rate ($Q_{pfr}$) based on said set value for a fluid removal rate ($Q_{pfr\_set}$), on said value of fluid to be removed from the patient ($V_{pfr\_need}$) over the time period ($T_{prosp}$) following the check point ($T_i$) and on the duration the time period ($T_{prosp}$) following the check point ($T_i$).

In a 32$^{nd}$ aspect according to any one of the preceding 5 aspects, the control procedure comprises calculating the updated value ($Q_{pfr\_new}$) for said fluid removal rate ($Q_{pfr}$) at check point ($T_i$) according to the formula:

$$Q_{pfr\_new}=[(T_{retro}+T_{prosp}) \cdot Q_{pfr\_set}-V_{pfr\_removed}]/T_{prosp}$$

where:
$Q_{pfr\_set}$ is the set value for fluid removal rate;
$V_{pfr\_removed}$ is the value of the fluid removed from the patient over time period ($T_{retro}$) preceding a check point ($T_i$);
$T_{retro}$ is a time period preceding check point ($T_i$);
$T_{prosp}$ is a time period following the check point ($T_i$);
($T_{retro}+T_{prosp}$) is the sum of the time period ($T_{retro}$) preceding check point ($T_i$) and of the time period ($T_{prosp}$) following the check point ($T_i$).

In a 33$^{rd}$ aspect according to any one of the preceding 6 aspects, each reference time interval ($\Delta T$) is of prefixed duration, beginning at prefixed start times ($T_{00}$; $T_{00}+\Delta T$; ...; $T_{00}+k \cdot \Delta T$) and ending at prefixed ending times ($T_{00}+\Delta T$; $T_{00}+2\Delta T$; ...; $T_{00}+(k+1) \cdot \Delta T$).

In a 34$^{th}$ aspect according to the preceding aspect the control procedure comprises calculating the updated value ($Q_{pfr\_new}$) for said fluid removal rate ($Q_{pfr}$) at check point ($T_i$) comprised between a start time ($T_{00}+k \cdot \Delta T$) and an end time $T_{00}+(k+1) \cdot \Delta T$ according to the formula:

$$Q_{pfr\_new}=(\Delta T \cdot Q_{pfr\_set}-V_{pfr(0)})/[(T_{00}+(k+1) \cdot \Delta T)-T_i]$$

or $$Q_{pfr\_new}=(2 \cdot \Delta T \cdot Q_{pfr\_set}-V_{pfr(0)}-V_{pfr(k-1)})/[(T_{00}(k+1) \cdot \Delta T)-T_i]$$

where:
$Q_{pfr\_set}$ is the set value for fluid removal rate;
$V_{pfr(0)}$ is the value of the fluid removed from the patient over time window running from ($T_{00}+k \cdot \Delta T$) to check point ($T_i$);
$V_{pfr(k-1)}$ is the value of the fluid removed from the patient over time window running from ($T_{00}+(k-1) \cdot \Delta T$) to ($T_{00}+k \cdot \Delta T$); [($T_{00}+(k+1) \cdot \Delta T$)-$T_i$] is the duration of time period following the check point ($T_i$);
$\Delta T$ is the reference time interval.

In a 35$^{th}$ aspect according to any one of the preceding 8 aspects, the control procedure comprises:
determining an effective portion ($T_{eff}$) of said the time period ($T_{prosp}$; [$T_{00}+(k+1)-\Delta T)-T_i$]) following the check point ($T_i$), during which it is forecasted that the ultrafiltration actuator will be actually pulling fluid from the primary into the secondary chamber (4);
calculating the updated value ($Q_{pfr\_new}$) for said fluid removal rate ($Q_{pfr}$) using said effective portion ($T_{eff}$) in place of the duration the time period following the check point ($T_i$).

In a 36$^{th}$ aspect according to any one of the preceding 9 aspects the effective portion ($T_{eff}$) is calculated reducing the duration of said the time period following check point ($T_i$) by a quantity linked to the number of bag changes expected in the next time period.

In a 37$^{th}$ aspect according to any one of the preceding 10 aspects the effective portion ($T_{eff}$) is calculated reducing the duration of said the time period following check point ($T_i$) by a quantity linked to down times caused by alarm conditions.

In a 38$^{th}$ aspect according to any one of the preceding 7 aspects the effective portion ($T_{eff}$) is calculated reducing the duration of said the time period following check point ($T_i$) by a quantity 11 linked to down times caused by alarm conditions if the duration of the time period ($T_{prosp}$) following the check point ($T_i$) is greater than a prefixed duration, such as grater than 30 mins or grater than 60 mins.

In a 39$^{th}$ aspect according to any one of the preceding aspects, the process includes receiving the set value ($Q_{pfr\_set}$) for patient fluid removal rate from an operator's input or from a remote source communicatively connected to the control unit or for pre-storing said set value.

In a 40$^{th}$ aspect according to any one of the preceding 13 aspects, the process comprises executing the following steps before executing the control procedure:
display on a user interface an indicium prompting a user to select a set value ($Q_{pfr\_set}$) for the patient fluid removal rate ($Q_{pfr}$),
detect entry by the user of the set value ($Q_{pfr\_set}$) for the patient fluid removal rate ($Q_{pfr}$),
receive the entered set value ($Q_{pfr\_set}$) for the patient fluid removal rate ($Q_{pfr}$).

In a 41$^{th}$ aspect according to any one of the preceding 14 aspects, the apparatus is of the type disclosed in any one of aspects from the 15$^{th}$ to the 20$^{th}$.

In a 42$^{nd}$ aspect according to any one of the preceding 15 aspects the control procedure comprises comparing the calculated updated value ($Q_{pfr\_new}$) for said fluid removal rate ($Q_{pfr}$) against a maximum threshold value before using it for controlling the ultrafiltration actuator.

In a 43$^{rd}$ aspect according to any one of the preceding 16 aspects the control procedure comprises executing one or more of the following safety checks:
comparing the ratio between the calculated updated value and the set value for the patient fluid removal rate with a first boundary condition (typically to ±30%),
comparing the absolute difference between the calculated updated value and the set value for the patient fluid removal rate with a second boundary condition (typically by ±100 ml/h),
comparing the absolute difference between the calculated updated value and the set value for the patient fluid removal rate as a function of patient body weight with a third boundary condition (typically by 0.1 ml/min/kg),
wherein the control procedure comprises verifying that a prefixed number, optionally all, of said checks is positively passed before using the update value for controlling the ultrafiltration actuator.

In a 44$^{th}$ aspect according to any one of the preceding aspects the ultrafiltration actuator comprises a waste pump (17) acting on the effluent conduit (13), this latter leading to a waste container (14) configured for collecting fluid extracted from the secondary chamber (4);
at least one sensor (33) being associated to the waste container and being communicatively connected to the control unit, wherein the sensor is configured to:
determine the weight or the volume of the fluid in said waste container and
generate corresponding measurement signals ($W_i$) for the control unit, and wherein the process comprises the step of calculating the actual quantity of fluid removed from the patient ($V_{pfr}$) over the reference time interval based at least on said measurement signals ($W_i$) coming from the sensor.

In a 45$^{th}$ aspect according to the preceding aspect, the apparatus comprises one or more of the following containers:

a pre-dilution fluid container connected to the pre-dilution line (15), a post-dilution fluid container connected to the post-dilution fluid line (25), a dialysis fluid container connected to the dialysis fluid line (19), a pre-blood pump infusion fluid container connected to the pre-blood pump infusion (22) line, a respective weighing sensor (34, 37, 35, 36) associated to each one of the above fluid containers and connected to the control unit (10), wherein said process comprises receiving set values for one or more fluid flow rates selected in the group including a fluid flow rate ($Q_{eff}$) through the effluent line (13), a fluid flow rate ($Q_{rep}$, $Q_{pbp}$) through the infusion fluid line (15, 21, 25), a fluid flow rate ($Q_{dial}$) through the dialysis liquid fluid line (27), in addition to said fluid removal rate ($Q_{pfr}$) from the patient, weigh signals ($W_i$) from said weighing sensors and to control said pumps and said actuator based on said weight signals, the set values for said one or more fluid flow rates and for said fluid removal rate ($Q_{pfr}$) from the patient.

In a 46$^{th}$ aspect a data carrier including instructions executable by a control unit of a blood treatment (for instance of the blood treatment device of any one of aspects from 1$^{st}$ to 26$^{th}$ apparatus) is provided. The instructions are configured such that, when executed by the control unit, they cause execution of the process according to any one of the preceding aspects from 27$^{th}$ to 45$^{th}$.

In a 47$^{TH}$ aspect according to the preceding aspect the data carrier may be any support suitable for storing data, such as by way of non-limiting example: a RAM, a ROM, an EPROM, an optical or a magnetic disc, an electromagnetic wave, a mass memory storage device such as an Hard Disk or a flash memory bank.

DESCRIPTION OF THE DRAWINGS

Aspects of the invention are shown in the attached drawings, which are provided by way of non-limiting example, wherein.

DETAILED DESCRIPTION

Figure 1:
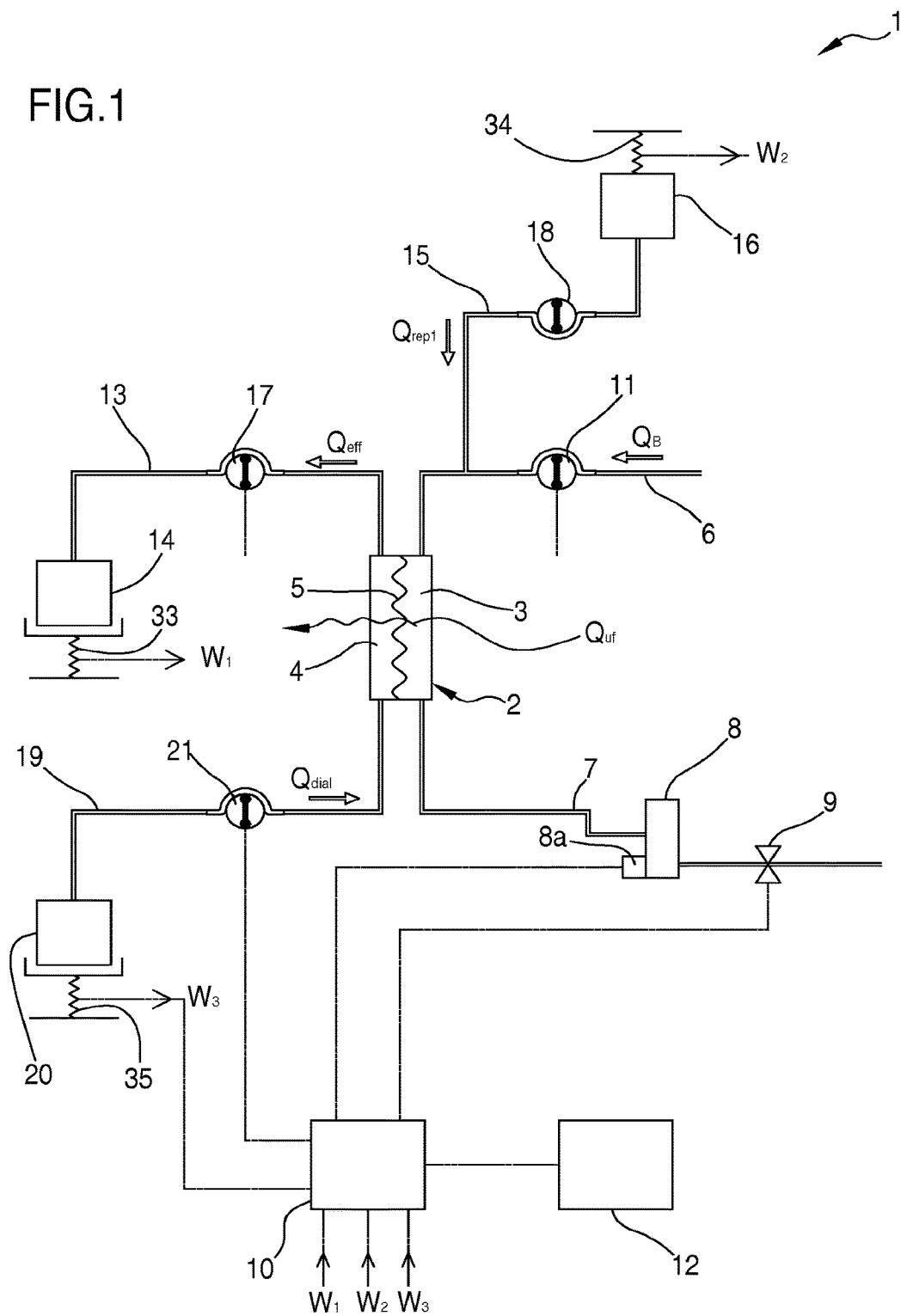
FIG. 1 shows a schematic diagram of a blood treatment apparatus according to one aspect of the invention.
Figure 2:
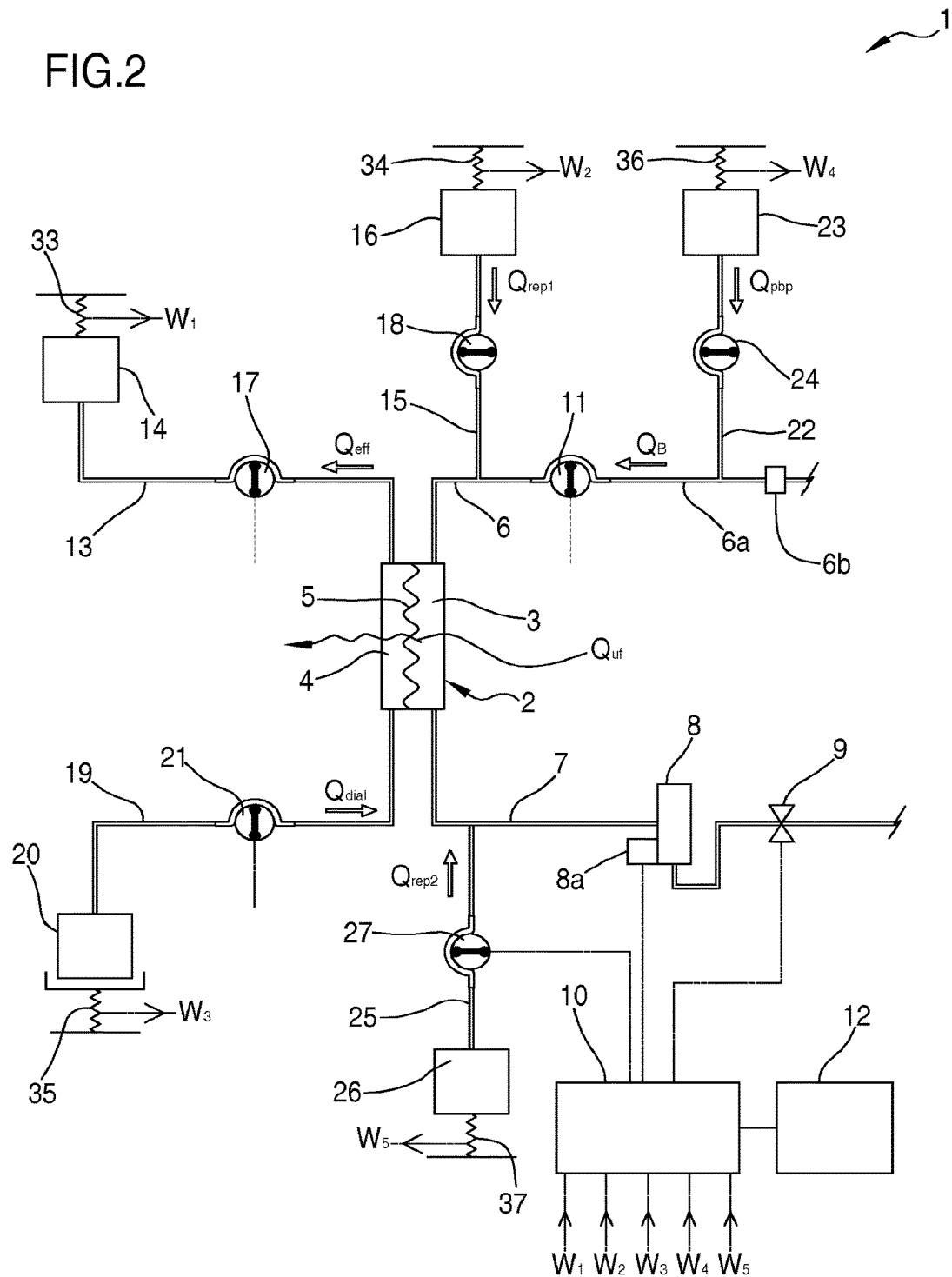
FIG. 2 shows a schematic diagram of an alternative embodiment of a blood treatment apparatus according to another aspect of the invention.
Figure 3:
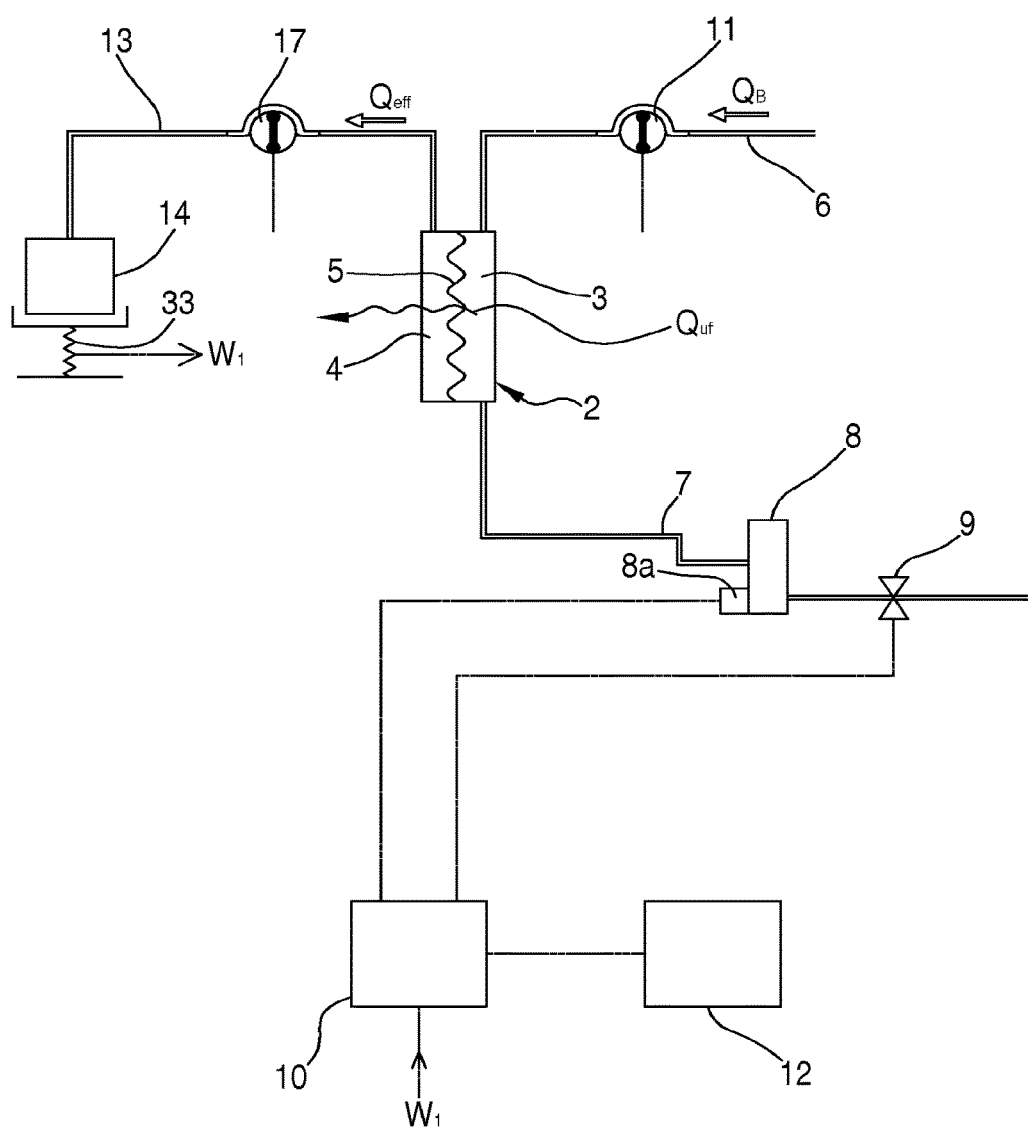
FIG. 3 shows a schematic diagram of a further alternative embodiment of a blood treatment apparatus according to another aspect of the invention.

FIGS. 1, 2 and 3 show exemplifying, and non limiting, embodiments of an apparatus for extracorporeal treatment of blood. Note that same components are identified by same reference numerals in FIGS. 1-3.

FIG. 1 shows an apparatus 1 designed for delivering any one of treatments like hemodialysis, hemofiltration, hemodiafiltration, and ultrafiltration.

In fact, the apparatus 1 comprises a filtration unit 2 having a primary chamber 3 and a secondary chamber 4 separated by a semi-permeable membrane 5; depending upon the treatment, the membrane of the filtration unit may be selected to have different properties and performances. A blood withdrawal line 6 is connected to an inlet of the primary chamber 3, and a blood return line 7 is connected to an outlet of the primary chamber 3. In use, the blood withdrawal line 6 and the blood return line 7 are connected to a needle or to a catheter or other access device (not shown) which is then placed in fluid communication with the patient vascular system, such that blood can be withdrawn through the blood withdrawal line, flown through the primary chamber and then returned to the patient's vascular system through the blood return line. An air separator, such as a bubble trap 8 may be present on the blood return line; moreover, a safety clamp 9 controlled by a control unit 10 may be present on the blood return line downstream the bubble trap 8. A bubble sensor 8a, for instance associated to the bubble trap 8 or coupled to a portion of the line 7 between bubble trap 8 and clamp 9 may be present: if present, the bubble sensor is connected to the control unit 10 and sends to the control unit signals for the control unit to cause closure of the clamp 9 in case one or more bubbles above certain safety thresholds are detected. As shown in FIG. 1, the blood flow through the blood lines is controlled by a blood pump 11, for instance a peristaltic blood pump, acting either on the blood withdrawal line (as shown in FIG. 1) or on the blood return line. An operator may enter a set value for the blood flow rate $Q_B$ through a user interface 12 and the control unit 10, during treatment, is configured to control the blood pump based on the set blood flow rate. The control unit may comprise a digital processor ((TIT) and memory (or memories), an analogical type circuit, or a combination thereof as explained in greater detail in below section dedicated to the 'control unit'. An effluent fluid line 13 is connected, at one end, to an outlet of the secondary chamber 4 and, at another end, to an effluent fluid container 14 collecting the fluid extracted from the secondary chamber. The embodiment of FIG. 1 also presents a pre-dilution fluid line 15 connected to the blood withdrawal line: this line 15 supplies replacement fluid from an infusion fluid container 16 connected at one end of the pre-dilution fluid line. Note that alternatively to the pre-dilution fluid line the apparatus of FIG. 1 may include a post-dilution fluid line (not shown in FIG. 1) connecting an infusion fluid container to the blood return line. Finally, as a further alternative (not shown in FIG. 1) the apparatus of FIG. 1 may include both a pre-dilution and a post infusion fluid line: in this case each infusion fluid line may be connected to a respective infusion fluid container or the two infusion fluid lines may receive infusion fluid from a same source of infusion fluid such as a same infusion fluid container. An effluent fluid pump 17 operates on the effluent fluid line under the control of said control unit 10 to regulate the flow rate $Q_{eff}$ across the effluent fluid line. Furthermore, an infusion pump 18 operates on the infusion line 15 to regulate the flow rate $Q_{rep}$ through the infusion line. Note that in case of two infusion lines (pre-dilution and post-dilution) each infusion line may cooperate with a respective infusion pump. The apparatus of FIG. 1, further includes a dialysis fluid line 19 connected at one end with a dialysis fluid container 20 and at its other end with the inlet of the secondary chamber 4 of the filtration unit. A dialysis liquid pump 21 works on the dialysis liquid fluid line under the control of said control unit 10, to supply fluid from the dialysis liquid container to the secondary chamber at a flow rate $Q_{dial}$.

The dialysis fluid pump 21, the infusion fluid pump 15 and the effluent fluid pump 17 are operatively connected to the control unit 10 which controls the pumps as it will be in detail disclosed herein below. The control unit 10 is also connected to the user interface 12, for instance a graphic user interface, which receives operator's inputs and displays the apparatus outputs. For instance, the graphic user interface 12 may include a touch screen, a display screen and hard keys for entering user's inputs or a combination thereof.

The embodiment of FIG. 2 shows an alternative apparatus 1 where the same components described for the embodiment of FIG. 1 are also presents and are identified by same reference numerals and thus not described again. Additionally, the apparatus 1 shown in FIG. 2 may present a further infusion line 22 connected, at one end, with a portion 6a of the blood withdrawal line 6 positioned upstream the blood pump 11 and, at its other end, with a further infusion fluid container 23, which for instance may contain a drug, or a regional anticoagulant such as a citrate solution, or a nutrients solution or other. This further infusion line is herein referred to as pre-blood pump infusion line 22. A pump 24, for instance a peristaltic pump controlled by control unit 10, may act on a segment of the pre-blood pump infusion line to regulate a pre-blood pump infusion rate $Q_{pbp}$.

The apparatus of FIG. 2, may also present a post-dilution line 25 (represented with dashed line) connected at one end with a further container 26 of infusion liquid and connected at its other end with the blood return line 7. A further pump 27, for instance a peristaltic pump, may act under the control of control unit 10 on the post-dilution line 25.

A third embodiment is shown in FIG. 3. The apparatus of FIG. 3 is an ultrafiltration apparatus comprising a filtration unit 2 (in this case an ultrafilter) having a primary chamber 3 and a secondary chamber 4 separated by a semi-permeable membrane 5. A blood withdrawal line 6 is connected to an inlet of the primary chamber 3, and a blood return line 7 is connected to an outlet of the primary chamber 3. As in the embodiment of FIG. 1, the blood withdrawal line 6 and the blood return line 7 are connected in use to a needle or to a catheter or other access device (not shown) which is then placed in fluid communication with the patient vascular system, such that blood can be withdrawn through the blood withdrawal line, flown through the primary chamber and then returned to the patient's vascular system through the blood return line. An air separator, such as a bubble trap 8 may be present on the blood return line; moreover, a safety clamp 9 controlled by a control unit 10 may be present on the blood return line downstream the bubble trap 8. A bubble sensor 8a, for instance associated to the bubble trap 8 or coupled to a portion of the line 7 between bubble trap 8 and clamp 9 may be present: if present, the bubble sensor is connected to the control unit 10 and sends to the control unit signals for the control unit to cause closure of the clamp 9 in case one or more bubbles above certain safety thresholds are detected. As shown in FIG. 1, the blood flow through the blood lines is controlled by a blood pump 11, for instance a peristaltic blood pump, acting either on the blood withdrawal line (as shown in FIG. 1) or on the blood return line. An operator may enter a set value for the blood flow rate $Q_B$ through a user interface 12 and the control unit 10, during treatment, is configured to control the blood pump based on the set blood flow rate. The control unit may comprise a digital processor (CPU) and memory (or memories), an analogical type circuit, or a combination thereof as explained in greater detail in below section dedicated to the 'control unit'. An effluent fluid line 13 is connected, at one end, to an outlet of the secondary chamber 4 and, at another end, to an effluent fluid container 14 collecting the fluid extracted from the secondary chamber. An effluent fluid pump 17 operates on the effluent fluid line under the control of said control unit 10 to regulate the flow rate $Q_{eff}$ across the effluent fluid line. The control unit 10 is also connected to the user interface 12, for instance a graphic user interface, which receives operator's inputs and displays the apparatus outputs. For instance, the graphic user interface 12 may include a touch screen, a display screen and hard keys for entering user's inputs or a combination thereof.

In each one of the above described embodiments an ultrafiltration actuator, comprising the effluent fluid pump 17, is inserted into the effluent fluid line 13 and configured to cause a transfer of fluid from the primary 3 to the secondary chamber 4; in practice, in the embodiment of FIG. 1 the control unit may drive the dialysis liquid pump 21, the infusion pump 18 and the effluent pump 17 such that $Q_{eff}$ is equal to $Q_{dial}+Q_{rep1}+Q_{pfr}$; in other words, the control unit drives the mentioned pumps so that the total flow rate flowing through the effluent line is made equal to the sum of the flow rate through the fresh dialysis liquid line, the flow rate through the replacement fluid line and the patient fluid removal rate which is to be imposed on the patient. In the embodiment of FIG. 2 the control unit may drive the dialysis liquid pump 21, the infusion pumps 18 and 27, the pre-blood pump infusion pump 24 and the effluent pump 17 such that $Q_{eff}$ is made equal to $Q_{dial}+Q_{rep1}+Q_{rep2}+Q_{pbp}+Q_{pfr}$; in the embodiment of FIG. 3, the flow $Q_{eff}$ equals $Q_{pfr}$ as there is no dialysate or infusion line. Although this is not shown in the enclosed figures, note that the extracorporeal blood treatment apparatus 1 (e.g. the apparatus 1 of FIG. 1 or 2 or 3) may include one or more syringe pumps: for instance a syringe pump connected to the blood withdrawal line 6 and a syringe pump connected to the blood return line 7; of course only one syringe may be used either connected to line 6 or to line 7. In this case, $Q_{eff}$ would be controlled to account for the flow rate delivered by said syringe pump(s). In FIGS. 1, 2, 3, $Q_{uf}$ represents the ultrafiltration flow rate, namely the flow rate passing through the semi-permeable membrane 5 ($Q_{pfr}=Q_{uf}$ in the case where there is pure ultrafiltration or pure hemodialysis, while $Q_{uf}=Q_{pfr}+Q_{rep1}$ and/or $+Q_{rep2}$ in case there are one or more infusions through respective fluid replacement lines).

In order to measure the quantity of fluid delivered or collected in each container, appropriate sensors are used. For instance, referring to FIGS. 1 and 2, the apparatus 1 also comprises a first scale 33 operative for providing weight information $W_1$ relative to the amount of the fluid collected in the effluent fluid container 14; a second scale 34 operative for providing weight information $W_2$ relative to the amount of the fluid supplied from the infusion fluid container 16; a third scale 35 operative for providing weight information $W_3$ relative to the amount of the fluid supplied from dialysis fluid container 20. In case more infusion lines would be present, as infusion lines 22 and 25 in FIG. 2, then a respective fourth and fifth scales 36 and 37 could be present to provide weight information $W_4$, $W_5$ relative to the amount of fluid supplied from infusion container 23 and from infusion container 26. In the apparatus of FIG. 3, a single scale 33 is present which is operative for providing weight information relative to the amount of the fluid collected in the effluent fluid container 14. The scales are all connected to the control unit 10 and provide said weight information $W_i$ for the control unit to determine the actual quantity of fluid in each container as well as the actual flow rate of fluid supplied by or received in each container. The control unit may also be configured to receive weight information $W_i$ from the first scale and, depending upon the selected treatment and type of apparatus, from one or more of the other the scales and to control the flow rate through the effluent fluid line, the infusion fluid line (if present), the dialysis fluid line (if present) by controlling the respective pumps based on said weight information W and on initial set values.

From a structural point of view one or more, all containers 14, 16, 20, 23 may be disposable plastic containers, for instance bags which are hang on a support carried by the respective scale. All lines and the filtration unit may also be plastic disposable components which may be mounted at the beginning of the treatment session and then disposed of at the end of the treatment session. Pumps, e.g. peristaltic pumps, have been described as means for regulating fluid flow through each of the lines; however it should be noted that other flow regulating means could alternatively be adopted such as for example valves or combinations of valves and pumps. The scales may comprise piezoelectric sensors, or strain gauges, or spring sensors, or any other type of transducer able to sense forces applied thereon. Although the examples in the figures show use of scales for determining the amount of fluid in the respective containers and for allowing calculation of the respective flow rates through the various lines, it should be noted that volumetric sensors for determining flow rates or combinations of mass and volumetric sensors may alternatively be adopted.

Operation

Figure 4:
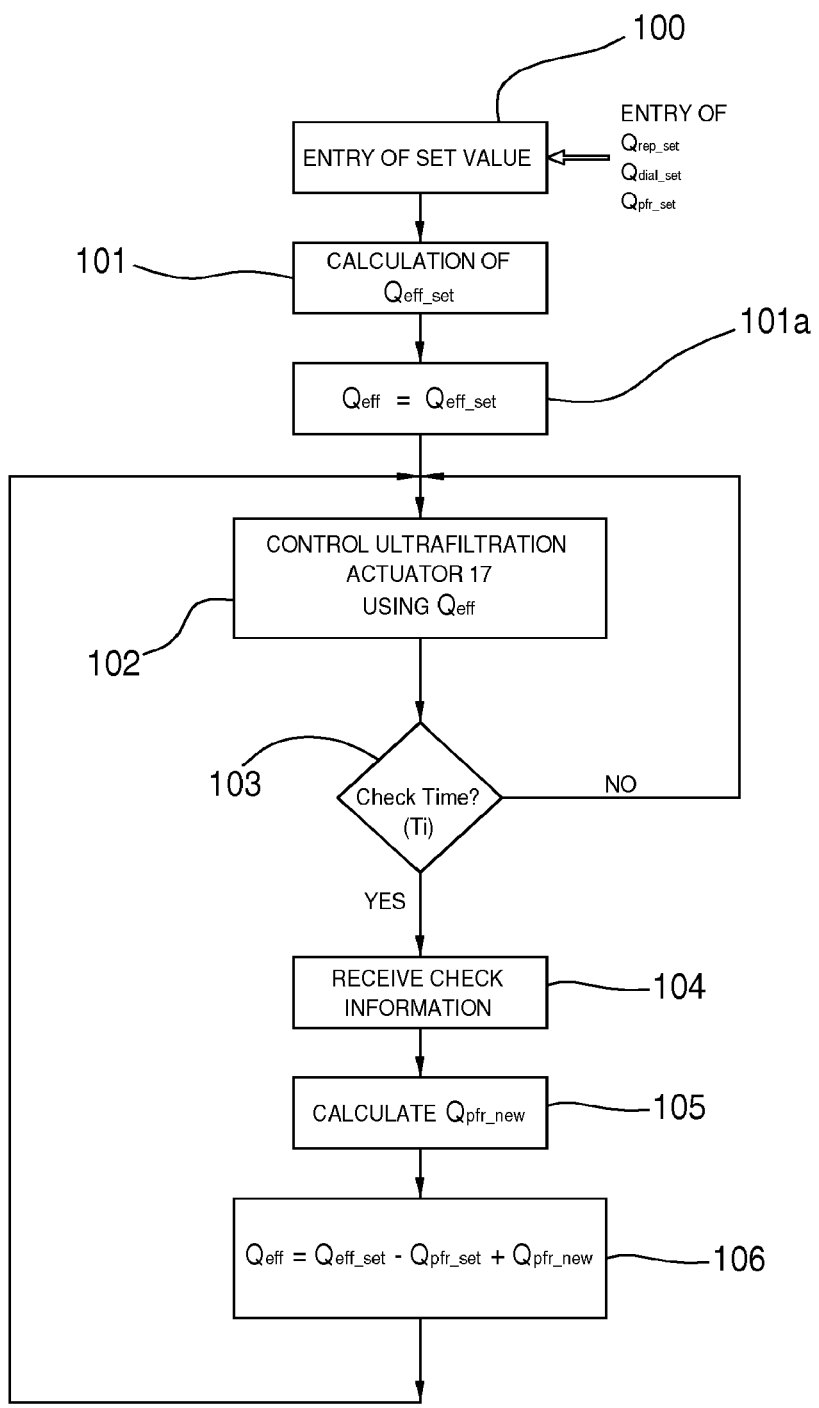
FIG. 4 shows a block diagram of a procedure executable by a control unit according to a further aspect of the invention, FIG. 5 graphically shows a first example of a control procedure according to aspects of the invention, FIG. 6 graphically shows a second example of a control procedure according to aspects of the invention, and FIG. 7 graphically shows a third example of a control procedure according to aspects of the invention.

Reference is made by way of non limiting example to the flowchart of FIG. 4. The control unit 10 is configured to control the ultrafiltration actuator (e.g. by controlling at least the effluent pump 17) based on a set value $Q_{pfr\_set}$ and to control the other pumps (such as pumps 18, 21, 24, 27 and the syringe(s)) if present based on set values initially set by an operator or pre-stored in the machine or received from a source external to the machine; for instance, with reference to FIG. 4, the control unit 10 may receive (step 100) set values for one or more of the flow rates $Q_{rep\_set}$ to be imposed through the infusion lines (when present), the set value $Q_{dial\_set}$ to be imposed through the dialysis liquid line (when present) and the set value $Q_{pfr\_set}$ for the patient fluid removal rate which is a desired value for the rate of fluid removal from the patient which is to be maintained during treatment. In the case of the apparatus of FIG. 3, the control unit 10 would be only receive the set value for the patient fluid removal rate $Q_{pfr\_set}$ and would be configured to control the ultrafiltration actuator based on said set value $Q_{pfr\_set}$. Then, the control unit may calculate the value $Q_{eff\_set}$ (step 101):

$$Q_{eff\_set} = Q_{dial\_set} + Q_{rep\_set} + Q_{pfr\_set} \quad (1)$$

Note that in case there is a pre-blood pump infusion line either the user shall enter a set value $Q_{pbp\_set}$ for the flow rate $Q_{pbp}$ of the respective pump 22, or the control unit is configured to calculate the set value $Q_{pbp\_set}$ as a function of the set blood flow rate $Q_{B\_set}$. In any case, if a pre-blood pump infusion line is present, the set flow rate is considered in equation (1) above and added at second member as follows:

$$Q_{eff\_set} = Q_{dial\_set} + Q_{rep\_set} + Q_{pbp\_set} + Q_{pfr\_set} \quad (2).$$

Of course, in case there is no infusion line and no dialysis line then equation (2) becomes:

$$Q_{eff\_set} = Q_{pfr\_set} \quad (3).$$

Then, the control unit uses the calculated $Q_{eff\_set}$ as value of the effluent flow rate $Q_{eff}$ (step 101a) which is used to control the flow of fluid through the effluent line. In detail, the control unit may control (step 102) each of the infusion pumps and the dialysis pump such that the actual flow rate matches the respective set flow rate and may control the effluent pump 17 (or ultrafiltration actuator) such that the actual flow rate through the effluent line matches the calculated value $Q_{eff\_set}$. In other words, once the $Q_{eff\_set}$ has been calculated as a function of $Q_{pfr\_set}$, then $Q_{eff\_set}$ may be used as $Q_{eff}$ to control the ultrafiltration actuator, e.g. the effluent pump 17 in the examples of FIGS. 1-3.

The control unit 10 is also configured to execute at check points $T_i$ (step 103) during patient treatment a control procedure comprising the steps 104, 105 and 106 as schematically shown in the flow chart of FIG. 4.

The control unit 10 may be configured for re-executing the control procedure at a plurality of check points $T_i$ during patient treatment: various criteria may be adopted to identify the check points $T_i$. For instance the control procedure may be repeated at periodic check points or at check points separated by time intervals following a prescribed rule (i.e. the time intervals between consecutive check points may not be all equal but nevertheless follow a prescribed rule). According to a further alternative the control procedure may be activated at check points triggered by specific events, such as a downtime of the machine due to a bag change or other reason, setting of a new set value $Q_{pfr\_set}$ for patient fluid removal rate, or setting of a new set value for any one of the flow rates $Q_{rep\_set}$, $Q_{pbp\_set}$ through the infusion lines (when present), the set value $Q_{dial\_set}$ to be imposed through the dialysis liquid line (when present).

Going now into the details of the exemplifying embodiment of FIG. 4, the control procedure comprises the following steps.

Step 104: receiving one check information selected in the group of:

a. a value of fluid removed from the patient over a time period preceding a check point $T_i$; this value may be calculated or measured by the scale or scales.

b. an effective time portion, of said time period preceding a check point, during which said ultrafiltration actuator is operated; this value may be measured by the apparatus taking detecting all intervals when the machine or the treatment is stopped, e.g. due to an alarm or due to a bag change or due to a change of the disposable set or due to other reasons.

c. a down time portion, of said time period preceding a check point T during which said ultrafiltration actuator is not operated; this value may be measured by the apparatus taking detecting all intervals when the machine or the treatment is stopped, e.g. due to an alarm or due to a bag change or due to a change of the disposable set or due to other reasons.

Step 105: calculating an updated value $Q_{pfr\_new}$ for said fluid removal rate $Q_{pfr}$ as a function of said set value for a fluid removal rate $Q_{pfr\_set}$ and of said check information. In most cases where the machine or the treatment has been interrupted in the period preceding a, the new value $Q_{pfr\_new}$ is higher than the set value $Q_{pfr\_set}$. Note, however, that there may be cases (e.g. if there is a flow delivery problem on dialysate or replacement) where too much fluid could have been extracted in the period preceding a check point: in such a situation the new value $Q_{pfr\_new}$ is smaller than the set value $Q_{pfr\_set}$.

Steps 106: after calculation of said updated value $Q_{pfr\_new}$, the control unit is configured for calculating a new $Q_{eff}$ for then returning to step 102.

At step 102 the control unit controls the ultrafiltration actuator (and the other pumps if present as above described in connection with step 102) as a function of said new $Q_{eff}$ and therefore as a function of the updated value $Q_{pfr\_new}$ of new Of the fluid removal rate. The control may use one of algorithms (1) or (2) or (3) depending upon the apparatus configuration, adopting $Q_{pfr\_new}$ new in place of $Q_{pfr\_set}$.

The control with the updated value may start immediately after the check point and last until a subsequent check point.

Here below some implementing examples are provided in order to exemplify the operation of apparatuses according to the invention. In below examples it is assumed that the set patient fluid flow rate $Q_{pfr\_set}$ is not changed in the time period preceding a check point.

EXAMPLE 1

Figure 5:
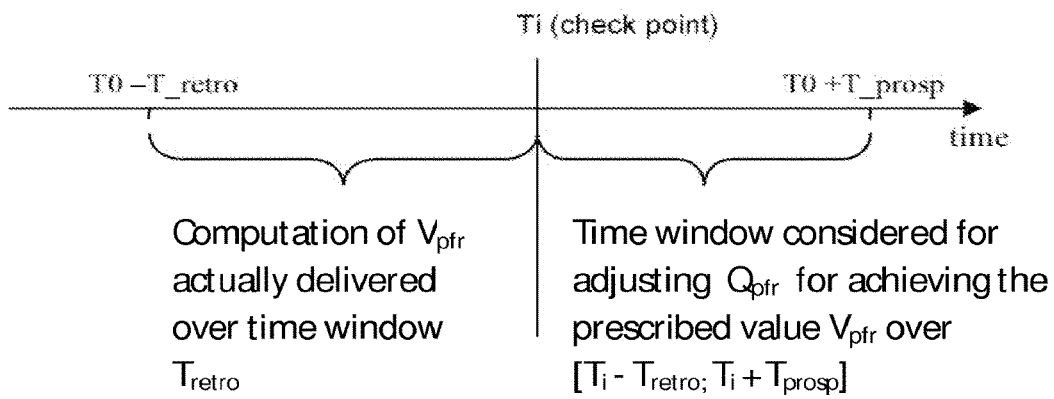

FIG. 5 shows a first example of implementation of the control procedure which has been described herein above.

In this embodiment, the control procedure comprises:
determining a value of the fluid removed from the patient $V_{pfr\_removed}$ over a time period $T_{retro}$ preceding a check point $T_i$;
determining a value of fluid to be removed from the patient $V_{pfr\_need}$ over a time period $T_{prosp}$ following the check point $T_i$ in order to achieve the set value $Q_{pfr\_set}$ for fluid removal rate $Q_{pfr}$ over the sum of the time period $T_{retro}$ preceding check point $T_i$ and of the time period $T_{prosp}$ following the check point ($T_i$); in FIG. 5, $T_{retro}$ is equal to $T_{prosp}$ although this may be a preferred option, it should be noted that $T_{retro}$ may also be different from $T_{prosp}$
calculating the updated value $Q_{pfr\_new}$ for said fluid removal rate $Q_{pfr}$ based on the set value for a fluid removal rate $Q_{pfr\_set}$, on the value of fluid to be removed from the patient $V_{pfr\_need}$ over the time period $T_{prosp}$ following the check point ($T_i$) and on the duration the time period $T_{prosp}$ following the check point $T_i$.

For example the following formula may be adopted for the calculation of $Q_{pfr\_new}$:

$$Q_{pfr\_new} = (T_{retro} + T_{prosp}) \cdot Q_{pfr\_set} - V_{pfr\_removed})/T_{prosp} \quad (4)$$

where:
$Q_{pfr\_set}$ is the set value for fluid removal rate;
$V_{pfr\_removed}$ is the value of the fluid removed from the patient over time period $T_{retro}$ preceding a check point $T_i$;
$T_{retro}$ is a time period preceding check point $T_i$;
$T_{prosp}$ is a time period following the check point $T_i$;
($T_{retro} + T_{prosp}$) is the reference time interval which is the sum of the time period $T_{retro}$ preceding check point $T_i$ and of the time period $T_{prosp}$ following the check point $T_i$.

The 'check point' $T_i$ when instantaneous $Q_{pfr\_new}$ is computed may be done:
after each treatment interruption (down time),
on a periodic basis,
each time the a flow rate setting is changed,
by time $T_i + T_{prosp}$.

In the context of patient fluid removal management, relevant values for $T_{retro}$ and $T_{prosp}$ may be in the range of 1 to 6-8 hours.

Applying the above algorithm to the apparatus of FIG. 3 assuming that:

the operator initially sets a $Q_{pfr\_set} = 100$ ml/h,
$T_{retro}$ and $T_{prosp}$ both equal to 4 h,
the fluid actually removed $V_{pfr\_removed}$ from the patient as measured by scale 33 (in case the apparatuses of FIGS. 1 and 2 would be used then information from all scales would be received by the control unit) over time period $T_{retro} = 4$ h preceding check point $T_1$ is $V_{pfr\_removed} = 390$ ml,
then applying formula (4) above:

$$Q_{pfr\_new} = \Delta T \cdot Q_{pfr\_set} - V_{pfr\_removed})/T_{prosp} = [(4+4) \cdot 100 - 390]/4 = 102.5 \text{ ml/h}$$

Thus, the control unit 10 will control the pump 17 based on the new calculated value of 102.5 ml/h during the 4 h following the first check point.

EXAMPLE 2

Figure 6:
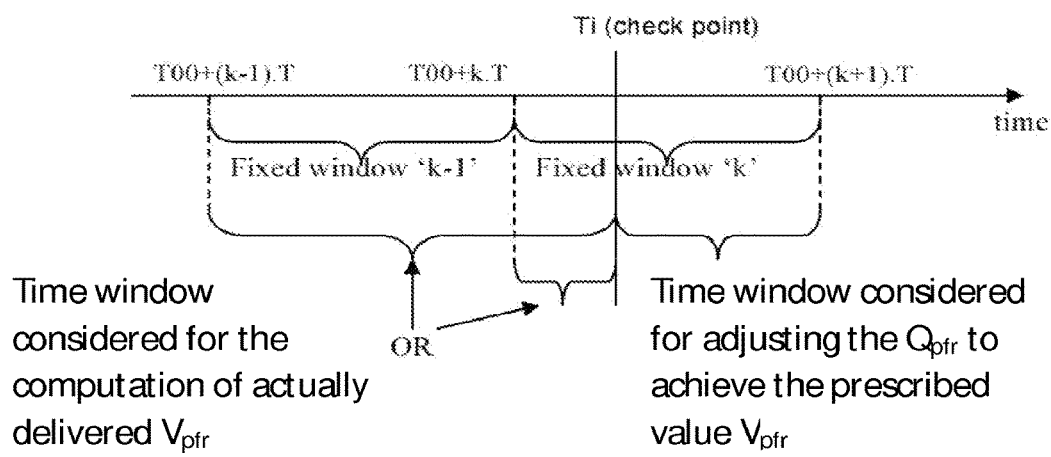

FIG. 6 shows a second example of implementation of the control procedure which has been described herein above.

In this case, the procedure aims at achieving the most accurate Patient Fluid Removal over predefined time periods. In this example, periods of constant duration $\Delta T$ are prefixed, beginning at a prefixed time TOO:
$T_{00}$; $T_{00} + \Delta T$; ... ; $T_{00} + k \cdot \Delta T$
and ending at prefixed ending times
$T_{00} + \Delta T$; $T_{00} + 2\Delta T$; ... ; $T_{00} + (k+1) \cdot \Delta T$.

In this variant, the control unit 10 aims at delivering the exact patient fluid removal prescription over predefined time windows, such as matching with staff shifts or simply 'round hours' (13:00, 14:00, 15:00 ... ).

The 'check point' $T_i$ when instantaneous $Q_{pfr\_new}$ is computed may be done:
at each treatment interruption (down time),
at each time a flow rate setting is changed,
at each predefined time window limit (T00+k·T), According to this variant, the control procedure comprises calculating the updated value $Q_{pfr\_new}$ for said fluid removal rate $Q_{pfr}$ at check point $T_i$ comprised between a start time $T_{00} + k \cdot \Delta T$ and an end time $T_{00} + (k+1) \cdot \Delta T$ according to the formula:

$$Q_{pfr\_new} = (\Delta T \cdot Q_{pfr\_set} - V_{pfr(0)})/[(T_{00} + (k+1) \cdot \Delta T) - T_i] \quad (5)$$

or according to the formula (which takes into account the volume of fluid removed in a further time window):

$$Q_{pfr\_new} = (2 \cdot \Delta T \cdot Q_{pfr\_set} - V_{pfr(0)} - V_{pfr(k-1)})/[(T_{00} + (k+1) \cdot \Delta T) - T_i] \quad (6)$$

where:
$Q_{pfr\_set}$ is the set value for fluid removal rate;
$V_{pfr(0)}$ is the value of fluid removed from patient over time window running from $(T_{00} + k \cdot \Delta T)$ to check point ($T_i$);
$V_{pfr(k-1)}$ is the value of fluid removed from patient over time window running from $(T_{00} + (k-1) \cdot \Delta T)$ to $(T_{00} + k \cdot \Delta T)$;
$[(T_{00} + (k+1) \cdot \Delta T) - T_i]$ is the duration of time period following the check point ($T_i$);
$\Delta T$ is the duration of the reference time interval.
Note:
Formula 5 is equivalent to formula 4 with:
$T_{retro} + T_{prosp} = \Delta T$
$T_{prosp} = (T_{00} + (k+1) \cdot \Delta T) - T_i$
Formula 6 is equivalent to formula 4 with:
$T_{ram} + T_{prosp} = 2 \cdot \Delta T$
$T_{prosp} = (T_{00} + (k+1) \cdot \Delta T) - T_i$
Applying the above algorithm to the apparatus of FIG. 3 assuming that:

the operator initially sets a $Q_{pfr\_set}$=100 ml/h;
Predefined time windows: 0:00; 4:00; 8:00; 12:00; 16:00; 20:00;
Check time $T_i$: 10:30,
the fluid actually removed over [4:00; 8:00] as measured by scale 33 (of course in case the apparatuses of FIGS. 1 and 2 would be used then information from all scales would be received by the control unit) is $V_{pfr(k-1)}$=396 ml;
the fluid actually removed over [4:00; 10:30] as measured by scale 33 (of course in case the apparatuses of FIGS. 1 and 2 would be used then information from all scales would be received by the control unit) is $V_{pfr(0)}$=245 ml,
then applying formula (6) above:

$$Q_{pfr\_new}=(2\cdot 4\cdot 100-245-396)/(12-10.5)=106.0 \text{ ml/h}$$

Thus, the control unit 10 will control the pump 17 based on the new calculated value of 106.0 ml/h during the 1.5 h following the check point at 10.30 in order to achieve the desired patient fluid removal by 12.00.

Anticipation of Down Times

Performance of the previous algorithms may be further enhanced when anticipating 'future' down times.

Several types of down-times may be estimated:
related to bag management: flow rate and bag volume data available to the system allow anticipating the number of bag changes which will occur over the period of interest; corresponding down time of the ultrafiltration actuator may then be derived using an assumption of the time used for changing a bag; such an estimate may derive from general statistical data or statistics more specific to the system in use and the local handling processes;
related to alarms: a simple alarm down time coefficient may be applied to estimate for the down times related to alarms interrupting the ultrafiltration actuator. Again such a coefficient may be built in the system or derived from statistics specific on the system in use.

By calculating the impact of the above down times it is possible to account for the effective portion $T_{eff}$ of the time period after check time $T_i$ during which it is forecasted that the ultrafiltration actuator will be actually pulling fluid from the primary into the secondary chamber 4. This allows further correcting the value of the new calculated patient fluid removal rate.

In practice, the control procedure described above may comprises a step of determining an effective portion $T_{eff}$ of said the time period $T_{prosp}$ or $(T_{00}+(k+1)\cdot \Delta T)-\Delta T_i$ following the check point $T_i$. Then, the updated value $Q_{pfr\_new}$ for the fluid removal rate $Q_{pfr}$ is calculated by the control unit using $T_{eff}$ in place of the duration the time period following the check point $T_i$, i.e. in place of Tprosp or $(T_{00}+(k+1)\cdot \Delta T)-T_i$.

EXAMPLE 3

The following example is similar to Example 2 (reference is made to FIGS. 3 and 6) and shows calculation and use of the effective portion $T_{en}$ which is determined in this case by reducing the duration of the time period following check point $T_i$ by a first quantity linked to a hag change average time expected to be spent in the next time period and by a second quantity linked to down times caused by alarm conditions.

Applying algorithm (6) to the apparatus of FIG. 3 assuming that:

the operator initially sets a $Q_{pfr\_set}$=100 ml/h;
Predefined time windows: 0:00; 4:00; 8:00; 12:00; 16:00; 20:00;
Check time $T_i$: 10:30,
the fluid actually removed over [4:00; 8:00] as measured by scale 33 is $V_{pfr(k-1)}$=396 ml;
the fluid actually removed over [4:00; 10:30] as measured by scale 33 is $V_{pfr(0)}$=245 ml;
Number of bag changes planned over [10:30; 12:00]: $N_{change\_bag}$=2;
Mean time for changing a bag: $T_{change\_bag}$=100 s;
Alarm down time coefficient: $K_{alarm}$=1.7%,
Thus, the effective run time of 'prospective' time window [10:30; 12:00] is:

$$T_{eff}=1.5-0.017\cdot 1.5-2\cdot (100/3600)=1.42 \text{ h}$$

It should be noted that in calculating $T_{eff}$, where $T_{prosp}$ becomes small (e.g. <30 minutes) the predictive term due to alarms may be ignored.

Then applying formula (6) using the calculated $T_{eff}$:

$$Q_{pfr\_new}=(2\cdot 4\cdot 100-245-396)/(1.42)=112.1 \text{ ml/h}$$

Thus, the control unit 10 will control the pump 17 based on the new calculated value of 112.1 ml/h during the 1.5 h following the check point at 10.30 in order achieve the most accurate delivery of the desired patient fluid removal over the time periods [4:00; 8:00] and [8:00; 12:00]. According to the criteria used for deciding on check points, this flow rate will be further adjusted at least twice before the current time period [8:00; 12:00] is elapsed (2 planned bag changes).

EXAMPLE 4

Figure 7:
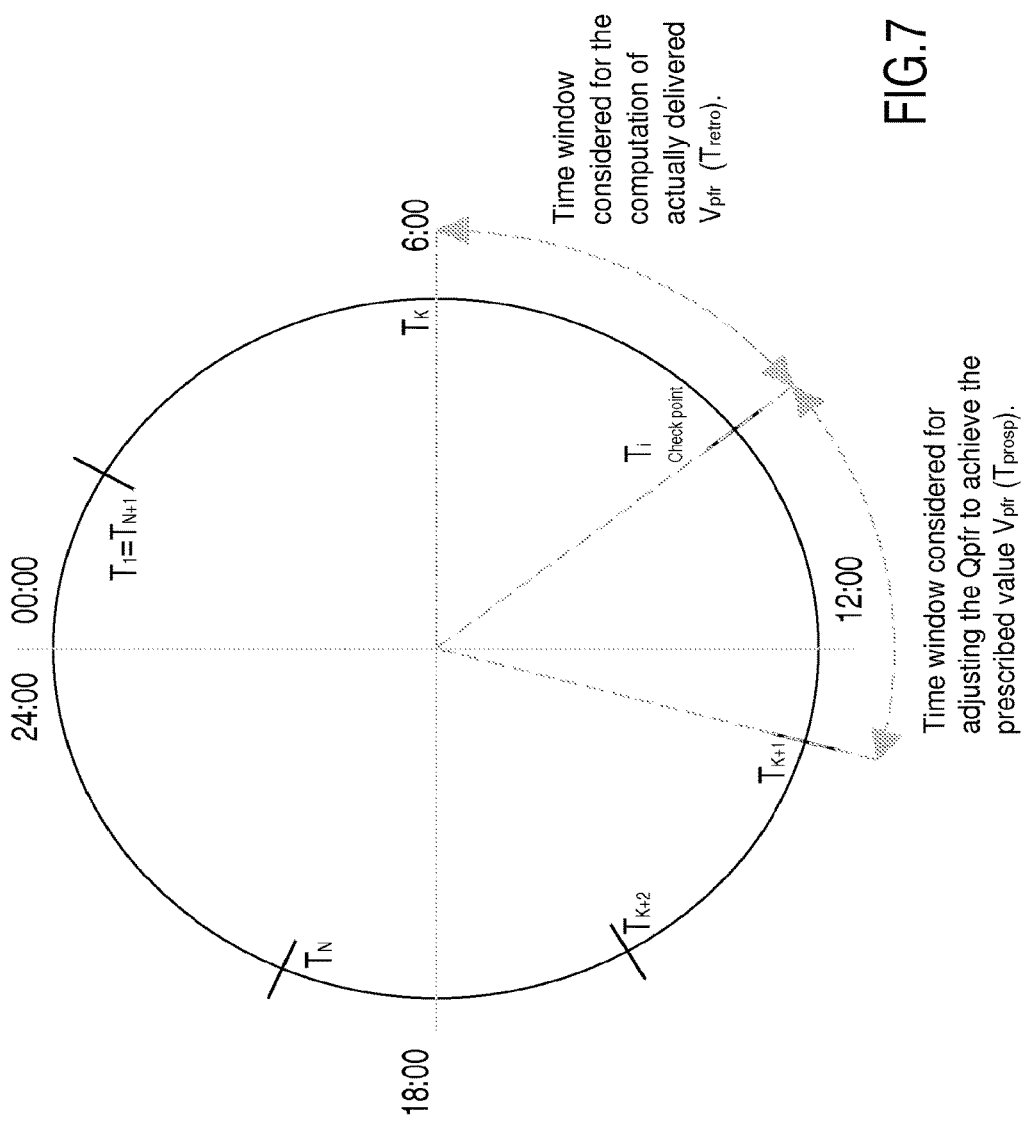

FIG. 7 shows another example of implementation of the control procedure which has been described herein above.

In this case, and as in example 2, the procedure aims at achieving the most accurate Patient Fluid Removal over predefined time periods. However, in this example, the time periods are defined around the clock and may be of different durations.

N clock times between 0:00 and 24:00 ($T_1$, $T_2$, ... $T_k$, ... $T_N$) define N time periods [$T_k$, $T_{k+1}$] (for k=1 to N and $T_{N+1}$=$T_1$).

In this variant, the control unit 10 aims at delivering the exact patient fluid removal prescription over each predefined time window, such as matching with staff shifts.

The 'check point' Ti when instantaneous $Q_{pfr\_new}$ is computed may be done:
at each treatment interruption (down time),
at each time a flow rate setting is changed,
at each predefined clock time Tk.

According to this variant, the control procedure comprises calculating the updated value $Q_{pfr\_new}$ for said fluid removal rate $Q_{pfr}$ at check point $T_i$ comprised between a start time $T_k$ and an end time $T_{k+1}$ according to the formula:

$$Q_{pfr\_new}=[(T_{k+1}-T_k)\cdot Q_{pfr\_set}-V_{pfr(0)}]/(T_{k+1}-T_i) \quad (7)$$

where:
$Q_{pfr\_set}$ is the set value for fluid removal rate;
$V_{pfr(0)}$ is the value of fluid removed from patient over time window running from clock time $T_k$ to check point ($T_i$);
$T_{k+1}-T_k$ matches with $T_{retro}+T_{prosp}$;
$T_{k+1}-Ti$ matches with $T_{prosp}$;
Applying the above algorithm (again refer to FIG. 7) and assuming that:
the operator initially sets a $Q_{pfr\_set}$=100 ml/h;
Predefined clock times: 6:00; 13:00; 20:00;
Check time $T_i$: 11:12;

The fluid actually removed over [6:00; 11:12] as measured by scale 33 (of course in case the apparatuses of FIGS. 1 and 2 would be used then information from all scales would be received by the control unit) is $V_{pfr(k-1)}$=508 ml;

No bag change expected before next predefined clock time $T_2$=13:00;

Mean time for changing a hag: $T_{change\_bag}$=100 s;

Alarm down time coefficient: $K_{alarm}$=1.5%, the effective run time $T_{eff}$ of 'prospective' time window [11:12; 13:00] is:

$$T_{eff}=(13.0-11.2)-0.015\cdot(13.0-11.2)-0\cdot(100/3600)= 1.773 \text{ h}$$

Then, applying formula (7) above:

$$Q_{pfr\_new}=[(13.0-6.0)\cdot-100-508]/1.773=108.3 \text{ ml/h}$$

Thus, the control unit 10 will control the pump 17 based on the new calculated value of 108.3 ml/h from the 11:12 check point in order to achieve the desired patient fluid removal by 13.00.

Safety Features

The apparatus described above may include one or more of the following safety features.

For instance safety features below disclosed may play an important role after a therapy interruption of several tens of minutes, e.g. change of the disposable tubing or substitution of filter set associated with the apparatus, temporary patient disconnection due to any reason. These situations may lead to relatively high Qpfr_new values which if actuated with no safety checks might lead to problems for the treated patient.

The control procedure executed by the control unit 10 may include a step of requesting the user, for instance via the user interface 12, to confirm that the calculated updated value $Q_{pfr\_new}$ for said fluid removal rate $Q_{pfr}$ is acceptable before using it for controlling the ultrafiltration actuator. In practice the control unit would in this case wait for a user confirmation before actually using the calculated updated value $Q_{pfr\_new}$ for controlling pump 17.

The control procedure may also include comparing the calculated updated value $Q_{pfr\_new}$ for said fluid removal rate ($Q_{pfr}$) against a maximum threshold value before using it for controlling the ultrafiltration actuator. In practice in case the calculate value would be too high either a lower value is used or an alarm condition is generated or a warning signal sent to the operator e.g. via user interface 12.

The control procedure may comprise executing one or more of the following further safety checks:
- comparing the ratio between the calculated updated value and the set value for the patient fluid removal rate with a first boundary condition (typically to ±30%),
- comparing the absolute difference between the calculated updated value and the set value for the patient fluid removal rate with a second boundary condition (typically by ±100 ml/h),
- comparing the absolute difference between the calculated updated value and the set value for the patient fluid removal rate as a function of patient body weight with a third boundary condition (typically by 0.1 ml/min/kg).

If a prefixed number of said checks is positively passed, for instance if all checks are passed, the update value $Q_{pfr\_new}$ is used for controlling the ultrafiltration actuator.

Note that the control unit is may also be configured for allowing setting of one or more boundary conditions in order to customize the apparatus to specific needs or patients.

Control Unit

As already indicated the apparatus according to the invention makes use of at least one control unit. This control unit may comprise a digital processor (CPU) with memory (or memories), an analogical type circuit, or a combination of one or more digital processing units with one or more analogical processing circuits. In the present description and in the claims it is indicated that the control unit is "configured" or "programmed" to execute certain steps: this may be achieved in practice by any means which allow configuring or programming the control unit. For instance, in case of a control unit comprising one or more CPUs, one or more programs are stored in an appropriate memory: the program or programs containing instructions which, when executed by the control unit, cause the control unit to execute the steps described or claimed in connection with the control unit. Alternatively, if the control unit is of an analogical type, then the circuitry of the control unit is designed to include circuitry configured, in use, to process electric signals such as to execute the control unit steps herein disclosed.

The invention claimed is:

1. A process of controlling an apparatus for extracorporeal treatment of blood, the apparatus being of the type comprising: a filtration unit having a primary chamber and a secondary chamber separated by a semi-permeable membrane; a blood withdrawal line connected to an inlet of the primary chamber, and a blood return line connected to an outlet of the primary chamber said blood lines being designed to be connected to a patient cardiovascular system; a blood pump for controlling flow of blood through the blood lines; an effluent fluid line connected to an outlet of the secondary chamber; an ultrafiltration actuator connected to the effluent fluid line and configured to cause a transfer of fluid from the primary chamber to the secondary chamber, wherein the process comprises:
   controlling the ultrafiltration actuator based on a set value for a patient fluid removal rate, said set value being a setting imposed on the ultrafiltration actuator defining a rate of fluid removal from a patient,
   determining when the ultrafiltration actuator is operated or when the ultrafiltration actuator is not operated,
   executing, at check points during patient treatment, a control procedure comprising:
      receiving check information selected from the group of:
         an effective time portion of a time period preceding a check point during which said ultrafiltration actuator is operated,
         and a down time portion of a time period preceding a check point during which said ultrafiltration actuator is not operated,
      calculating an updated set value for said patient fluid removal rate as a function of said set value for the patient fluid removal rate and of said check information.

2. The process according to claim 1 wherein the control procedure further comprises, after calculating said updated value, controlling the ultrafiltration actuator after the check point as a function of said updated value for the fluid removal rate.

3. The process according to claim 1, wherein the process further comprises re-executing said control procedure at a plurality of check points during patient treatment, said plurality of check points comprising one or more check points selected from the group of:
   check points at regular intervals,
   periodic check points, check points triggered by a specific setting of a new set value for the patient fluid removal rate, check points triggered by a stop in the ultrafiltration actuator, and check points triggered each time a flow rate setting is changed.

4. The process according to claim 1, wherein the control procedure comprises:

determining a value of the fluid volume removed from the patient over the time period preceding the check point;

determining a value of fluid to be removed from the patient over a time period following the check point in order to achieve the set value for fluid removal rate over a sum of the time period preceding the check point and of the time period following the check point;

calculating the updated value for said fluid removal rate based on said set value for the patient fluid removal rate, on said value of fluid to be removed from the patient over the time period following the check point and on the duration of the time period following the check point.

5. The process according to claim 4 wherein the control procedure comprises calculating the updated value for said fluid removal rate at the check point according to the formula:

$$Q_{pfr\_new} = [(T_{retro} + T_{prosp}) \cdot Q_{pfr\_set} - V_{pfr\_removed}] / T_{prosp}$$

where:

$Q_{pfr\_new}$ is the calculated updated value for said fluid removal rate;

$Q_{pfr\_set}$ is the set value for the fluid removal rate;

$V_{pfr\_removed}$ is the value of the fluid volume removed from the patient over the time period ($T_{retro}$) preceding the check point);

$T_{retro}$ is the time period preceding the check point;

$T_{prosp}$ is the time period following the check point;

($T_{retro} + T_{prosp}$) is the sum of the time period ($T_{retro}$) preceding the check point and the time period ($T_{prosp}$) following the check point.

6. The process according to claim 1, wherein the control procedure comprises calculating the updated value for said fluid removal rate at a selected check point-between a start time and an end time according to the formula:

$$Q_{pfr\_new} = (\Delta T \cdot Q_{pfr\_set} - V_{pfr(0)}) / [(T_{00} + (k+1) \cdot \Delta T) - T_i]$$

or $$Q_{pfr\_new} = (2 \cdot \Delta T \cdot Q_{pfr\_set} - V_{pfr(0)} - V_{pfr(k-1)}) / [(T_{00} + (k+1) \cdot \Delta T) - T_i]$$

where:

$Q_{pfr\_new}$ is the updated value for the fluid removal rate;

$Q_{pfr\_set}$ is the set value for the fluid removal rate;

($T_{00} + k \cdot \Delta T$) is the start time;

$T_{00} + (k+1) \cdot \Delta T$ is the end time;

$T_i$ is the selected check point;

$V_{pfr(0)}$ is the value of the fluid volume removed from the patient over a first time window running from the start time ($T_{00} + k \cdot \Delta T$) to the selected check point;

$V_{pfr(k-1)}$ is the value of the fluid volume removed from the patient over a second time window running from the start time ($T_{00} + (k-1) \cdot \Delta T$) to the end time ($T_{00} + k \cdot \Delta T$);

$[(T_{00} + (k+1) \cdot \Delta T) - T_i]$ is a duration of a time period following the selected check point;

$\Delta T$ is a reference time interval of prefixed duration.

7. The process according to claim 4, wherein the control procedure comprises:

determining an effective portion of said time period following the check point during which the ultrafiltration actuator will be pulling fluid from the primary chamber into the secondary chamber;

calculating the updated value for said fluid removal rate using said effective portion in place of the duration of the time period following the check point.

8. The process according to claim 7 wherein the effective portion is calculated by reducing the duration of the time period following the check point by a quantity linked to one or more of: a number of bag changes expected in a next time period, down times caused by alarm conditions, and down times caused by alarm conditions if the duration of the time period following the check point is greater than a prefixed duration.

9. The process according to claim 1, wherein the control procedure comprises comparing the calculated updated value for said fluid removal rate against a maximum threshold value before using the calculated updated value for said fluid removal rate for controlling the ultrafiltration actuator.

10. The process according to claim 1, wherein the control procedure comprises executing one or more of the following safety checks:

comparing a ratio between the calculated updated value and the set value for the patient fluid removal rate with a first boundary condition, comparing an absolute difference between the calculated updated value and the set value for the patient fluid removal rate with a second boundary condition, comparing the absolute difference between the calculated updated value and the set value for the patient fluid removal rate as a function of patient body weight with a third boundary condition, wherein the control procedure comprises verifying that a prefixed number of said safety checks is positively passed before using the updated value for controlling the ultrafiltration actuator.

11. A process of controlling an apparatus for extracorporeal treatment of blood, the apparatus being of the type comprising: a filtration unit having a primary chamber and a secondary chamber separated by a semi-permeable membrane; a blood withdrawal line connected to an inlet of the primary chamber, and a blood return line connected to an outlet of the primary chamber said blood lines being designed to be connected to a patient cardiovascular system; a blood pump for controlling flow of blood through the blood lines; an effluent fluid line connected to an outlet of the secondary chamber; an ultrafiltration actuator connected to the effluent fluid line and configured to cause a transfer of fluid from the primary chamber to the secondary chamber, wherein the process comprises:

controlling the ultrafiltration actuator based on a set value for a patient fluid removal rate, said set value being a setting imposed on the ultrafiltration actuator defining a rate of fluid removal from a patient, executing at check points during patient treatment a control procedure comprising:

receiving a check information selected from the group of:

an effective time portion of a time period preceding a check point during which said ultrafiltration actuator is operated, and a down time portion of a time period preceding a check point during which said ultrafiltration actuator is not operated;

calculating an updated set value for said patient fluid removal rate as a function of said set value for the patient fluid removal rate and of said check information;

after calculating said updated set value for the patient removal rate, controlling the ultrafiltration actuator after the check point as a function of said updated set value for the patient fluid removal rate.

12. The process according to claim 11, wherein the process further comprises re-executing said control procedure at a plurality of check points during patient treatment, said plurality of check points comprising one or more check points selected from the group of:

check points at regular intervals,
periodic check points,
check points triggered by a specific setting of a new set value for the patient fluid removal rate,
check points triggered by a stop in the ultrafiltration actuator, and
check points triggered each time a flow rate setting is changed.

13. The process according to claim 11, wherein the control procedure comprises:

determining a value of the fluid volume removed from the patient over a time period preceding the check point;
determining a value of fluid to be removed from the patient over a time period following the check point in order to achieve the set value for fluid removal rate over the sum of the time period preceding the check point and of the time period following the check point;
calculating the updated value for said fluid removal rate based on said set value for the patient fluid removal rate, on said value of fluid to be removed from the patient over the time period following the check point and on the duration of the time period following the check point, wherein calculating the updated value for said fluid removal rate comprises using the formula:

$$Q_{pfr\_new} = [(T_{retro} + T_{prosp}) \cdot Q_{pfr\_set} - V_{pfr\_removed}] / T_{prosp}$$

where:
$Q_{pfr\_new}$ is the updated value for the fluid removal rate;
$Q_{pfr\_set}$ is the set value for the fluid removal rate;
$V_{pfr\_removed}$ is the value of the fluid volume removed from the patient over the time period $T_{retro}$ preceding the check point;
$T_{retro}$ is a time period preceding the check point;
$T_{prosp}$ is a time period following the check point; and
$(T_{retro} + T_{prosp})$ is the sum of the time period ($T_{retro}$) preceding the check point and of the time period ($T_{prosp}$) following the check point.

14. The process according to claim 11, wherein the control procedure comprises calculating the updated value for said fluid removal rate at a selected check point between a start time and an end time according to the formula:

$$Q_{pfr\_new} = (\Delta T \cdot Q_{pfr\_set} - V_{pfr(0)}) / [(T_{00} + (k+1) \cdot \Delta T) - T_i]$$

or $$Q_{pfr\_new} = (2 \cdot \Delta T \cdot Q_{pfr\_set} - V_{pfr(0)} - V_{pfr(k-1)}) / [(T_{00} + (k+1) \cdot \Delta T) - T_i]$$

where:
$Q_{pfr\_new}$ is the updated value for the fluid removal rate;
$Q_{pfr\_set}$ value for the fluid removal rate;
$(T_{00} + k \cdot \Delta T)$ is the start time;
$T_{00} + (k+1) \cdot \Delta T$ is the end time;
$T_i$ is the selected check point;

$V_{pfr(0)}$ is the value of the fluid volume removed from the patient over a first time window running from the start time $(T_{00} + k \cdot \Delta T)$ to the selected check point $(T_i)$;
$V_{pfr(k-1)}$ is the value of the fluid volume removed from the patient over a second time window running from the start time $(T_{00} + (k-1) \cdot \Delta T)$ to the end time $(T_{00} + k \cdot \Delta T)$;
$[(T_{00} + (k+1) \cdot \Delta T) - T_i]$ is the duration of a time period following the selected check point $(T_i)$; and
$\Delta T$ is a reference time interval of a prefixed duration.

15. A process of controlling an apparatus for extracorporeal treatment of blood, the apparatus being of the type comprising: a filtration unit having a primary chamber and a secondary chamber separated by a semi-permeable membrane; a blood withdrawal line connected to an inlet of the primary chamber, and a blood return line connected to an outlet of the primary chamber said blood lines being designed to be connected to a patient cardiovascular system; a blood pump for controlling a flow of blood through the blood lines; an effluent fluid line connected to an outlet of the secondary chamber; an ultrafiltration actuator connected to the effluent fluid line and configured to cause a transfer of fluid from the primary chamber to the secondary chamber, wherein the process comprises:

controlling the ultrafiltration actuator based on a set value for a patient fluid removal rate, said set value being a setting imposed on the ultrafiltration actuator defining a rate of fluid removal from a patient,
executing at check points during patient treatment a control procedure comprising:
receiving a check information selected from the group of:
a value of fluid removed from the patient over a time period preceding a check point,
an effective time portion of a time period preceding a check point during which said ultrafiltration actuator is operated, and
a down time portion of a time period preceding a check point during which said ultrafiltration actuator is not operated;
determining an effective portion of a time period following the check point during which the ultrafiltration actuator will be pulling fluid from the primary chamber into the secondary chamber;
calculating an updated set value for the patient fluid removal rate as a function of:
said set value for the patient fluid removal rate,
said effective portion of the time period following the check point, and
said check information;
after calculating said updated set value for the patient fluid removal rate, controlling the ultrafiltration actuator after the check point as a function of said updated set value for the patient fluid removal rate.

16. The process according to claim 15 wherein the effective portion is calculated by reducing the duration of the time period following check point by a quantity linked to one or more of:

a number of bag changes expected in a next time period;
down times caused by alarm conditions; and
down times caused by alarm conditions if the duration of the time period following the check point is greater than a prefixed duration.

17. The process according to claim 15, wherein the control procedure comprises comparing the calculated updated value for said fluid removal rate against a maximum threshold value before using the calculated updated value for controlling the ultrafiltration actuator.

18. The process according to claim 15, wherein the control procedure comprises executing one or more of the following safety checks:
- comparing a ratio between the calculated updated value and the set value for the patient fluid removal rate with a first boundary condition,
- comparing an absolute difference between the calculated updated value and the set value for the patient fluid removal rate with a second boundary condition, and
- comparing the absolute difference between the calculated updated value and the set value for the patient fluid removal rate as a function of patient body weight with a third boundary condition,
- wherein the control procedure comprises verifying that a prefixed number of said safety checks is positively passed before using the updated value for controlling the ultrafiltration actuator.

* * * * *

UNITED STATES PATENT AND TRADEMARK OFFICE
CERTIFICATE OF CORRECTION

PATENT NO. : 10,258,726 B2
APPLICATION NO. : 15/240231
DATED : April 16, 2019
INVENTOR(S) : Dominique Pouchoulin It is certified that error appears in the above-identified patent and that said Letters Patent is hereby corrected as shown below:

In the Claims

Column 23, Line 45, "$Q_{pfr\_new} = (\Delta T \cdot Q_{pfr\_set} - V_{pfr(0)}) / [(T_{00} + (k+1) \cdot \Delta T) - T]$" should read --$Q_{pfr\_new} = (\Delta T \cdot Q_{pfr\_set} - V_{pfr(0)}) / [(T_{00} + (k+1) \cdot \Delta T) - T_{i}]$--.

Signed and Sealed this
Twenty-fourth Day of September, 2019

Andrei Iancu
*Director of the United States Patent and Trademark Office*